US008221975B2

(12) United States Patent
Yoshida et al.

(10) Patent No.: US 8,221,975 B2
(45) Date of Patent: Jul. 17, 2012

(54) METHOD FOR DETECTION OF MICROORGANISM

(75) Inventors: Shinichi Yoshida, Fukuoka (JP); Takashi Soejima, Zama (JP)

(73) Assignee: Morinaga Milk Industry Co., Ltd., Minato-ku, Tokyo (JP)

( * ) Notice: Subject to any disclaimer, the term of this patent is extended or adjusted under 35 U.S.C. 154(b) by 29 days.

(21) Appl. No.: 12/445,506

(22) PCT Filed: Aug. 1, 2008

(86) PCT No.: PCT/JP2008/063865
§ 371 (c)(1),
(2), (4) Date: Apr. 14, 2009

(87) PCT Pub. No.: WO2009/022558
PCT Pub. Date: Feb. 19, 2009

(65) Prior Publication Data
US 2011/0053790 A1    Mar. 3, 2011

(30) Foreign Application Priority Data

Aug. 16, 2007   (JP) ................................. 2007-212366

(51) Int. Cl.
*C12Q 1/68* (2006.01)
(52) U.S. Cl. ........................................................ 435/6.1
(58) Field of Classification Search ........................ None
See application file for complete search history.

(56) References Cited

U.S. PATENT DOCUMENTS

2003/0049673 A1 * 3/2003 Atkinson et al. .................. 435/6
2003/0203374 A1    10/2003 Rudi

FOREIGN PATENT DOCUMENTS

RU          2 258 740     2/2005
WO    WO 02/052034        7/2002

OTHER PUBLICATIONS

Nogva et al. ( Biotechniques. Apr. 2003;34(4):804-8, 810, 812-3).*
Decision of Grant issued Jul. 29, 2010 to a corresponding Russian patent application No. 2009120527.
Rudi, et al. "Detection of Viable and Dead *Listeria monocytogenes* on Gouda-like Cheeses by Real-time PCR," *Letters in Applied Microbiology*, vol. 40, pp. 301-306, 2005.
Rudi, et al. "Use of Ethidium Monoazide and PCR in Combination for Quantification of Viable and Dead Cells in Complex Samples," *Applied and Environmental Microbiology*, vol. 71, pp. 1018-1024, 2005.
Guy, et al. "A Rapid Molecular-based Assay for Direct Quantification of Viable Bacteria in Slaughterhouses," *Journal of Food Protection*, vol. 69, No. 6, pp. 1265-1272, 2006.
Nogva, et al. "Ethidium Monoazide for DNA-based Differentiation of Viable and Dead Bacteria by 5'-Nuclease PCR," *BioTechniques*, vol. 34, pp. 804-813, 2003.
Rudi, et al. "Development and Application of New Nucleic Acid-based Technololgies for Microbial Community Analyses in Foods," *International Journal of Food Microbiology*, vol. 78, pp. 171-180, 2002.
Soejima, et al. "Photoactivated Ethidium Monazide Directly Cleaves Bacterial DNA and is Applied to PCR for Discrimination of Live and Dead Bacteria," *Microbiology and Immunology*, vol. 51, pp. 763-775, 2007.
International Search Report dated Oct. 1, 2008.
Nocker, et al. "Comparison of propidium monoazide with ethidium monoazide for differentiation of live vs. dead bacteria by selective removal of DNA from dead cells," *Journal of Microbiological Methods* vol. 67, pp. 310-320, 2006.
Pan, et al. "Enumeration of Viable *Listeria monocytogenes* Cells by Real-Time PCR with Propidium Monoazide and Ethidium Monoazide in the Presence of Dead Cells," *Applied and Environmental Microbiology*, vol. 73, No. 24, pp. 8028-8031, Dec. 2007.
Supplementary European Search Report, dated Mar. 6, 2012 issued to corresponding European application No. 08792078.1.

* cited by examiner

*Primary Examiner* — Christopher M. Babic
(74) *Attorney, Agent, or Firm* — Knobbe, Martens, Olson & Bear, LLP

(57) ABSTRACT

A live cell of microorganism in a test sample is detected by the following steps of: a) adding a cross-linker capable of cross-linking a DNA by irradiation with light having a wavelength of 350 nm to 700 nm to the test sample; b) irradiating the test sample to which the cross-linker is added with light having a wavelength of 350 nm to 700 nm; c) removing the cross-linker contained in the test sample irradiated with light; d) adding a medium to the test sample from which the cross-linker is removed and incubating the test sample; e) adding again the cross-linker capable of cross-linking a DNA by irradiation with light having a wavelength of 350 nm to 700 nm to the incubated test sample; f) irradiating the test sample to which the cross-linker is added with light having a wavelength of 350 nm to 700 nm; g) extracting a DNA from the test sample and amplifying a target region of the extracted DNA by a nucleic acid amplification method; and h) analyzing the amplified product.

9 Claims, 5 Drawing Sheets

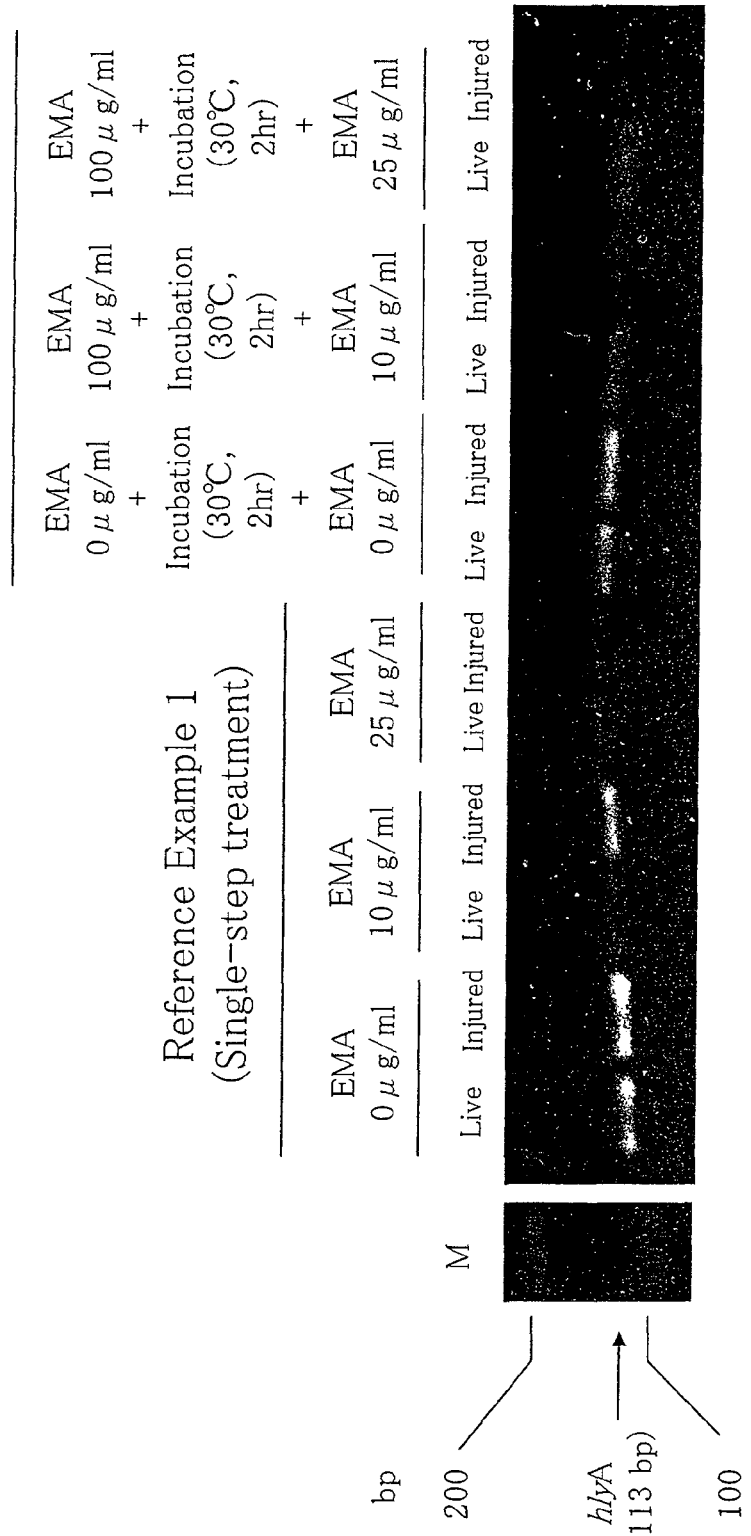
[Fig. 1]

[Fig. 2]

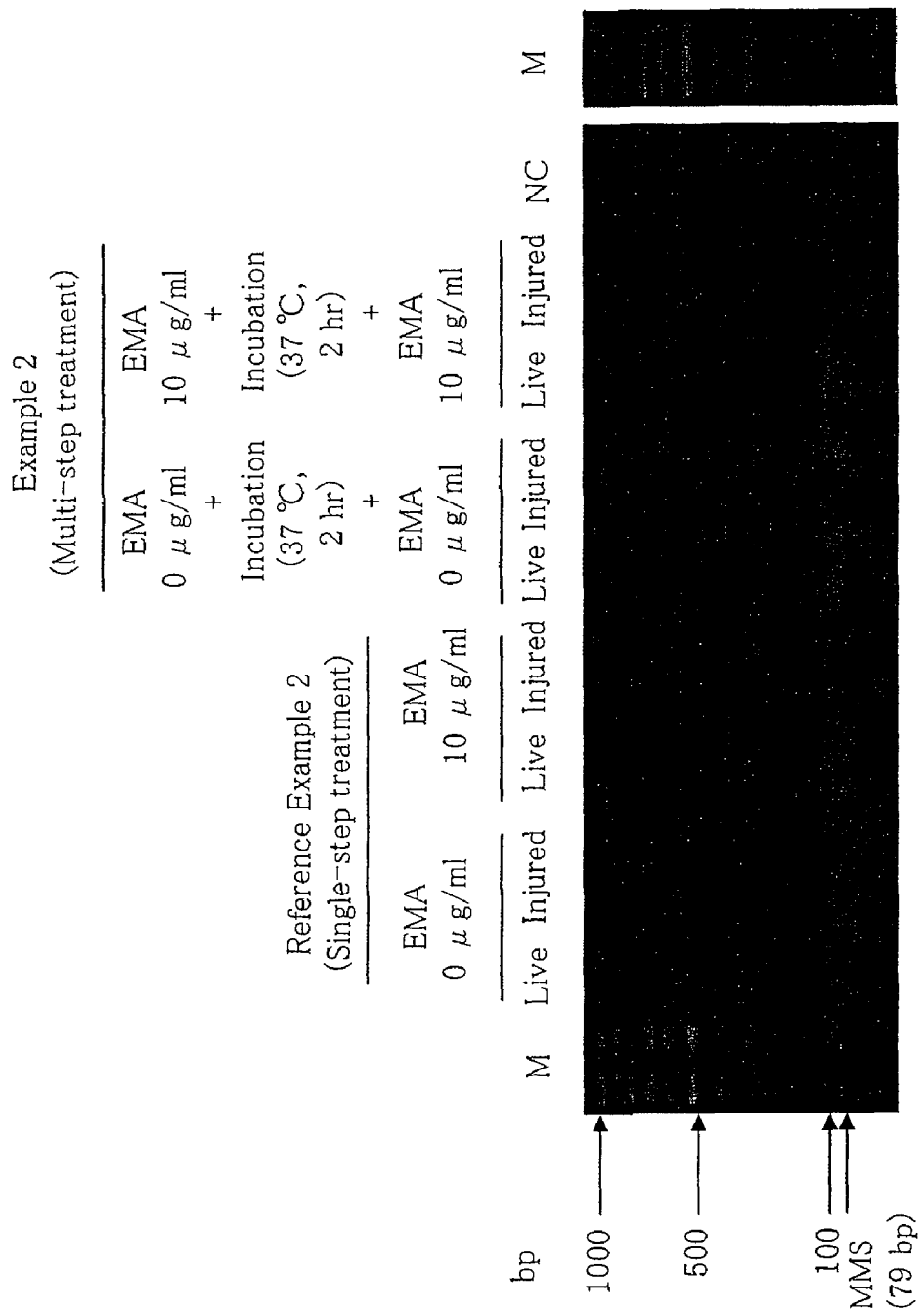
[Fig. 3]

[Fig. 4]

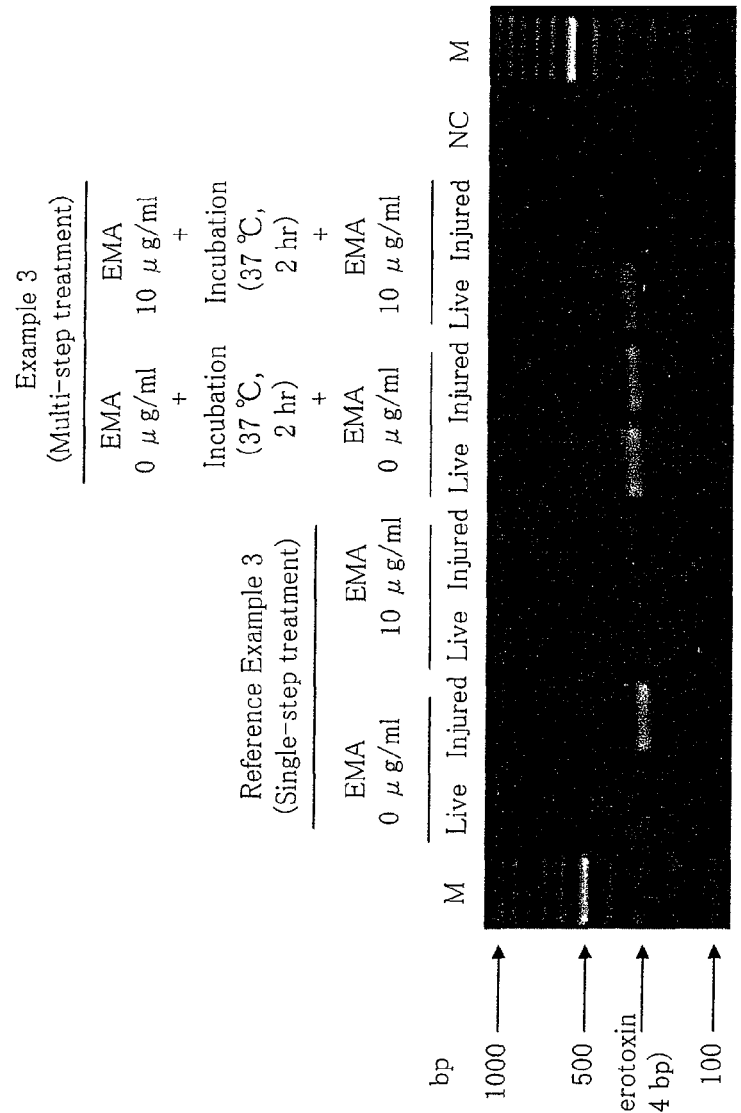
[Fig. 5]

METHOD FOR DETECTION OF MICROORGANISM

CROSS-REFERENCE TO RELATED APPLICATIONS

This application is the U.S. National Phase under 35 U.S.C. §371 of International Application PCT/JP2008/063865, filed Aug. 1, 2008, which was published in a non-English language, which claims priority to Japanese Patent Application No. 2007-212366, filed Aug. 16, 2007.

TECHNICAL FIELD

The present invention relates to a method and kit for detecting a microorganism contained in a foodstuff, a biological sample and an environmental sample such as industrial water and tap water. More precisely, the present invention relates to a method and kit for detection of a microorganism that enable selective detection of live cells of a microorganism contained in a foodstuff, a biological sample and an environmental sample such as industrial water and tap water.

BACKGROUND ART

The plate culture method has been conventionally used for measurement of total live bacterial counts in foodstuffs, biological samples or environmental samples. However, the plate culture method requires time of about two days to obtain a result.

Because of the improvements of sterilization techniques and processing techniques for foodstuffs, needs for distinguishing live states of microorganisms from dead states of microorganisms existing in test samples are increasing even for the cases where the cells exist in an extremely small amount. In the fields of food sanitation inspection and clinical test, in particular, as a quick method for detecting bacteria, it is attempted to determine presence or absence of bacteria or quantify bacteria by amplifying genes specific to the bacteria by PCR to such an amount that the genes can be visually observed. However, if a bacterial DNA is targeted, the background of dead bacteria originally contained in the test sample is also detected, and therefore a positive result obtained by PCR does not necessarily suggest the presence of live bacteria. Therefore, the current situation in the fields of food sanitation and clinical test is that PCR is not used widely, although it is a highly sensitive and quick technique.

In these days, it is attempted to detect and quantify only live cells of microorganism in a test sample by preparing cDNA with reverse transcriptase for mRNA as a target and performing PCR with primers specific to various bacteria. However, in this method, the reverse transcription of mRNA of dead cells itself is not inhibited, and when $10^4$ cfu/ml or $10^4$ cfu/g or more of dead cells are contained in the test sample, background of the dead cells is detected. Therefore, this method cannot be said to be sufficient as a method for determining the live and dead states.

Specifically, as a method for distinguishing live state from dead states of microorganisms such as bacteria using the PCR method, the methods described in Patent document 1 and 2 have been disclosed. However, the following problems remain in these methods for distinguishing live and dead states of microorganisms such as bacteria using the PCR method.

As for the technique disclosed in Patent document 1, examples are mentioned for distinction of dead cells contained in boiled foodstuffs subjected to high temperature long time sterilization at 100° C. for 10 to 30 minutes, and microorganisms contained in foodstuffs subjected to ethanol sterilization or formaldehyde sterilization. However, especially the treatment of the latter type, there are not foodstuffs actually subjected to such pasteurization treatments. Moreover, there are not supposed detection of only live microorganisms subjected to the currently major sterilization method in the food industry, low temperature long time pasteurization (LTLT pasteurization), high temperature short time pasteurization (HTST pasteurization), or ultra high temperature pasteurization (UHT, pasteurization), and detection of only live specific pathogenic bacteria in clinical specimens of infectious disease patients administered with antibiotics. Moreover, in the case of a test sample of a foodstuff or clinical specimen containing dead cell background at a concentration of $10^4$ cfu/ml or higher, the amounts of the final PCR amplification products derived from dead cells exceed the detection limit of the technique of Patent document 1, and therefore it is impossible to determine whether a positive response of a test sample obtained by PCR is derived from live cells or dead cells.

Further, as the technique of Patent document 2, disclosed is a method of distinguishing live cells from dead cells by utilizing relative decrease in RNA/DNA molar ratio of dead cells compared with that of live cells. In this method, the total RNA is extracted, complementary DNA is prepared by using a reverse transcription reaction, then PCR is performed to calculate the Ct value thereof, and the molar concentration of RNA is obtained by using a separately prepared calibration curve. Separately, a region of chromosomal DNA corresponding to that RNA is amplified by PCR to obtain the Ct value thereof, and the molar concentration of the chromosomal DNA is calculated on the basis of the calibration curve to obtain the RNA/DNA molar ratio. That is, the above procedure requires to perform troublesome extraction of total RNA and uses two steps of reverse transcription reaction and PCR. Therefore, this technique is inferior to usual PCR targeting DNA in quantification performance and quickness. Further, RNA is continuously produced in live cells, whereas RNA derived from dead cells is decomposed at an early stage. Therefore, the technique lacks stability. Furthermore, in a foodstuff or clinical specimen containing dead cells at a high concentration, only live cells of 1/10 of that concentration can be detected by this technique. Therefore, it is difficult to apply this technique in the fields of food sanitation inspection and clinical test, which require quickness, high sensitivity and accuracy.

Patent document 1: Domestic Laid-Open Publication of a Japanese translation of PCT Application (KOHYO) No. 2003-530118
Patent document 2: International Patent Publication WO2002/052034

DISCLOSURE OF THE INVENTION

Problems to be Resolved by the Invention

An object of the present invention is to provide a method for selectively detecting live cells (viable-and-culturable cells) of a microorganism contained in a foodstuff or biological sample in contrast to dead cells or injured cells (injured cells or viable-but-non-culturable cells (VNC cells)) of microorganism, that is, a quick detection method alternative to the culture method, but succeeding the characteristics of the culture method as they are, and a kit for performing the method.

Means of Solving the Problems

The inventors of the present invention have made extensive studies on a method of discriminating between life and death of microorganisms, which is applicable to various sterilization methods and is suitable for food sanitation inspections of high detection sensitivity, and on a method of detecting a specific pathogen in a patient with an infection in hospital or clinical practice. As a result, the inventors have found out that the evaluation can be performed rapidly by a method of distinguishing live cells of microorganism from injured cells of microorganism in a test sample, which comprises: treating a test sample with a cross-linker capable of cross-linking DNA by irradiation with light having a wavelength of 350 nm to 700 nm; irradiating the sample with light having a wavelength of 350 nm to 700 nm; removing the cross-linker; adding a medium suitable for culture for microorganism contained in the test sample and incubating the test sample for a certain period of time; treating the sample with the cross-linker again; irradiating the sample with light having a wavelength of 350 nm to 700 nm; and selectively amplifying a chromosomal DNA of the microorganism by nucleic acid amplification reaction. Thus, the present invention has been completed.

That is, the present invention provides a method of detecting a live cell of a microorganism in a test sample comprising the steps of:

a) adding a cross-linker capable of cross-linking a DNA by irradiation with light having a wavelength of 350 nm to 700 nm to the test sample;

b) irradiating the test sample to which the cross-linker is added with light having a wavelength of 350 nm to 700 nm;

c) removing the cross-linker contained in the test sample irradiated with light;

d) adding a medium to the test sample from which the cross-linker is removed and incubating the test sample;

e) adding again the cross-linker capable of cross-linking a DNA by irradiation with light having a wavelength of 350 nm to 700 nm to the incubated test sample;

f) irradiating the test sample to which the cross-linker is added with light having a wavelength of 350 nm to 700 nm;

g) extracting a DNA from the test sample and amplifying a target region of the extracted DNA by a nucleic acid amplification method; and h) analyzing the amplified product.

In the method, it is preferable to analyze the amplified product based on a standard curve, which is created by using a standard sample of the microorganism and shows a relationship between an amount of the microorganism and the amplified product.

Further, in the method, it is preferable to use a PCR, LAMP, SDA, LCR, or DNA microarray method as the nucleic acid amplification method.

In a preferred embodiment of the aforementioned method, PCR is performed by real-time PCR, and PCR and analysis of the amplified product are simultaneously performed.

Further, in the method, the test sample is preferably a food, a blood sample, an urine sample, a spinal fluid sample, a synovial fluid sample, a pleural effusion sample, industrial water, tap water, groundwater, river water or rainwater.

Further, in the method, it is preferable to select a cross-linker from the group consisting of ethidium monoazide, ethidium diazide, psolaren, 4,5',8-trimethyl psolaren, and 8-methoxy psolaren.

Further, in the method, the target region preferably has a length of 50 to 5,000 bases.

Further, in the method, the microorganism is preferably a pathogenic bacterium. In this aspect, it is preferred that the target region is a pathogenic gene.

Further, the present invention provides a kit for detecting a live cell of a microorganism in a test sample by a nucleic acid amplification method, comprising the following components:

a cross-linker capable of cross-linking a DNA by irradiation with light having a wavelength of 350 nm to 700 nm; a medium; and a primer(s) for amplifying a target region of a DNA of a microorganism, which is a detection target, by the nucleic acid amplification method.

In the kit, it is preferably a PCR, LAMP, SDA, LCR, or DNA microarray method as the nucleic acid amplification method.

In the kit, it is preferable to select the cross-linker from the group consisting of ethidium monoazide, ethidium diazide, psolaren, 4,5',8-trimethyl psolaren, and 8-methoxy psolaren.

BRIEF DESCRIPTION OF THE DRAWINGS

FIG. 1 An electrophoresis image illustrating band intensities of final amplified products of hlyA-PCR of *Listeria* (live cells and injured cells) treated by single-step treatment and multi-step treatment with a cross-linker (EMA).
Live: live *Listeria* cell
Injured: injured *Listeria* cell FIG. 2 An electrophoresis image illustrating band intensities of final amplified products of ompA-PCR of *Enterobacter sakazakii* (live cells and injured cells) treated by single-step treatment and multi-step treatment with the cross-linker (EMA).
Live: live *Enterobacter sakazakii* cell
Injured: injured *Enterobacter sakazakii* cell FIG. 3 An electrophoresis image illustrating band intensities of final amplified products of MMS-PCR of *Enterobacter sakazakii* (live cells and injured cells) treated by single-step treatment and multi-step treatment with the cross-linker (EMA).
Live: live *Enterobacter sakazakii* cell
Injured: injured *Enterobacter sakazakii* cell FIG. 4 An electrophoresis image illustrating band intensities of final amplified products of invA-PCR of *Salmonella* (live cells and injured cells) treated by single-step treatment and multi-step treatment with the cross-linker (EMA).
Live: live *Salmonella* cell
Injured: injured *Salmonella* cell FIG. 5 An electrophoresis image illustrating band intensities of final amplified products of enterotoxin-PCR of *Salmonella* (live cells and injured cells) treated by single-step treatment and multi-step treatment with the cross-linker (EMA).
Live: live *Salmonella* cell
Injured: injured *Salmonella* cell

DESCRIPTION OF THE PREFERRED EMBODIMENTS

Hereinafter, preferred embodiments of the present invention are described in detail. However, the present invention is not limited to the following preferred embodiments and may be modified within the scope of the present invention. The percentage in the present description is expressed as a percentage by mass unless otherwise specified.

A target to be detected by the method of the present invention includes all kinds of nucleic acids, specifically, single-stranded DNA, double-stranded DNA, single-stranded RNA, and double-stranded RNA, as long as the target can be amplified eventually. Of those, the detection target is preferably DNA, particularly preferably double-stranded DNA.

<1> Method of the Present Invention

A method of detecting a live cell of microorganism in a test sample comprising the steps of:

a) adding a cross-linker capable of cross-linking a DNA by irradiation with light having a wavelength of 350 nm to 700 nm to the test sample;

b) irradiating the test sample to which the cross-linker is added with light having a wavelength of 350 nm to 700 nm;

c) removing the cross-linker contained in the test sample irradiated with light;

d) adding a medium to the test sample from which the cross-linker is removed and incubating the test sample;

e) adding again the cross-linker capable of cross-linking a DNA by irradiation with light having a wavelength of 350 nm to 700 nm to the incubated test sample;

f) irradiating the test sample to which the cross-linker is added with light having a wavelength of 350 nm to 700 nm;

g) extracting a DNA from the test sample and amplifying a target region of the extracted DNA by a nucleic acid amplification method; and h) analyzing the amplified product.

In the specification of the present invention, the term "test sample" refers to an object containing live cells of microorganism to be detected. The test sample is not particularly limited as long as the presence of the microorganism can be detected by amplification of a specific region of chromosomal DNA by a nucleic acid amplification method. Preferred examples thereof include foods, blood samples, urine samples, spinal fluid samples, synovial fluid samples, pleural effusion samples, industrial water, tap water, groundwater, river water, and rainwater. In particular, preferred examples of the foods include: drinks such as soft drinks, carbonated soft drinks, supplement drinks, fruit juice drinks, and lactobacillus drinks (including concentrates and powders of these drinks); ice confectionery products such as ice creams, ice sherbets, and shaved ice; dairy products such as processed milk, milk drinks, fermented milk, and butter; enteral foods, fluid diets, milk for infant, sports drinks; and functional foods such as foods for specified health use and dietary supplements. In the present invention, the test sample may be any of such products or biological samples themselves or may be any of diluted or concentrated products thereof or any of products obtained by a pretreatment other than the method of the present invention. Examples of the pretreatment include heat treatment, filtration, and centrifugation.

Further, foreign substances such as cells other than microorganisms, protein colloidal particles, and lipids in the test sample may be removed or reduced by enzyme treatment or the like. In the case where the test sample is any of milk, dairy products, and foods produced from milk or dairy products, examples of the cells other than microorganisms in the test sample include bovine leukocytes and mammary epitheliocytes. Meanwhile, in the case where the test sample is any of biological samples such as blood samples, urine samples, spinal fluid samples, synovial fluid samples, and pleural effusion samples, examples of the cells include erythrocytes, leukocytes (such as granulocytes, neutrophils, basophils, monocytes, and lymphocytes), and thrombocytes.

The enzyme is not particularly limited as long as it can degrade the foreign substances and does not damage live cells of microorganism to be detected, and examples thereof include lipid-degrading enzymes and protein-degrading enzymes. Of those, one enzyme or two or more enzymes may be used, but both of the lipid-degrading enzyme and protein-degrading enzyme are preferably used.

Examples of the lipid-degrading enzymes include lipase and phosphatase, and examples of the protein-degrading enzymes include proteinase K and pronase.

The "microorganism" is an object to be detected by the method of the present invention, and is not particularly limited so long as it can be detected by nucleic acid amplification methods, and closs-linker act on live cells of the microorganism in a manner different from that for dead cells and injured cells of the microorganism. Preferred examples include bacteria, fungi, yeasts, and so forth. The bacteria include both gram-positive bacteria and gram-negative bacteria. Examples of the gram-positive bacteria include *Staphylococcus* bacteria such as *Staphylococcus epidermidis*, *Streptococcus* bacteria, *Listeria* bacteria such as *Listeria monocytogenes*, *Bacillus* bacteria such as *Bacillus cereus*, *Mycobacterium* bacteria, *Clostridium* bacteria such as *Clostridium botulinum* and *Clostridium perfringens* and so forth. Examples of the gram-negative bacteria include *Escherichia* bacteria such as *Escherichia coli*, *Enterobacter* bacteria such as *Enterobacter sakazakii*, *Citrobacter* bacteria such as *Citrobacter koseri*, and *Klebsiella* bacteria such as *Klebsiella oxytoca*, *Salmonella* bacteria, *Vibrio* bacteria, *Pseudomonas* bacteria, and so forth.

In the present invention, the "live cell" refers to a cell in a state that the cell can proliferate, and exhibits metabolic activities of the microorganism (viable-and-culturable state), when it is cultured under generally preferred culture conditions, and is a cell substantially free from injury of cell wall. As the metabolic activities mentioned above, ATP activity, esterase activity etc. can be exemplified.

The "dead cell" is a cell in a state that it cannot proliferate, and does not exhibit metabolic activities (dead state), even if it is cultured under an optimum culture condition. Moreover, it is in a state that although structure of cell wall is maintained, the cell wall itself is highly injured, and a nuclear stain agent exhibiting weak permeability such as propidium iodide can penetrate or permeate the cell wall.

The "injured cell" (injured cell or viable-but-non culturable cell) is a cell in a state that even when it is cultured under a generally preferred culture condition, it hardly proliferates because it is injured due to artificial stress or environmental stress, and it shows metabolic activities at a lower level compared with a live cell, but a significant level compared with a dead cell.

Detection of bacteria exhibiting the state of injured cell due to mild heat treatment or administration of antibiotics is attracting attention, in particular, in the field of food sanitation inspection and clinical test, and the present invention provides a method for detecting a microorganism, which enables not only detection of live cells, but also distinction of live cells from dead cells or injured cells.

The unit of cell number is usually cell number (cells)/ml for all of live cells, injured cells and dead cells. The number of live cells can be approximated with a number of formed colonies (cfu/ml (colony forming units/ml)) obtainable by culturing the cells under an optimum condition on a suitable plate medium. A standard sample of injured cells of microorganism can be prepared by, for example, subjecting a live cell suspension to a heat treatment, for example, a heat treatment in boiling water. The number of injured cells in such a sample can be approximated with cfu/ml in the live cell suspension before the heat treatment. Although time of the heat treatment in boiling water for preparing injured cells varies depending on type of microorganism, injured cells of the bacteria described in the examples, for example, can be prepared by a heat treatment of about 50 seconds. Further, a standard sample of injured cells of microorganism can also be prepared by a treatment with an antibiotic. In such a case, the cell number of the injured cells can be approximated based on the number of formed colonies (cfu/ml) observed when the cells are cultured under an optimum condition on a suitable plate medium, that is, a live cell suspension is treated with an antibiotic, then the antibiotic is removed, transmittance of visible light (wavelength: 600 nm) through the suspension, i.e., turbidity of the suspension, is measured, and the measured turbidity can be compared with that of a live cell suspension of a known live cell density to calculate the number of injured cells treated with the antibiotic.

The method of the present invention is for detection of live cells of microorganism, and cells of the microorganism distinguished from live cells may be injured cells or dead cells.

In the present invention, the "detection of live cells" includes both determination of presence or absence of live cells in a test sample and determination of amount of live cells in a test sample. The amount of live cells is not limited to an absolute amount, and may be a relative amount with respect to that in a control sample.

Hereafter, the method of the present invention will be explained for each step.

(1) Step a)

A test sample was treated with a cross-linker capable of cross-linking a DNA by irradiation with light having a wavelength of 350 nm to 700 nm.

The cross-linker to be used in the present invention is one which can intercalate into chromosomal DNA and bind covalently to the chromosomal DNA by irradiation with light having a wavelength of 350 nm to 700 nm, to thereby cross-link DNA molecules.

The cross-linker preferably has different actions on live cells of microorganism compared with injured or dead cells of microorganism and somatic cells such as bovine leukocytes, leukocytes, or thrombocytes. More specifically, the cross-linker is preferably one which can more easily pass through cell walls of injured or dead cells of microorganism and cell membranes of somatic cells such as bovine leukocytes, leukocytes, or thrombocytes compared with cell walls of live cells of microorganism.

Examples of the cross-linker include ethidium monoazide, ethidium diazide, psolaren, 4,5',8-trimethyl psolaren (PMA), and 8-methoxy psolaren. One kind of those cross-linkers may be used alone, or two or more kinds thereof may be used in combination.

The conditions of the treatment with the cross-linker may be appropriately set. For example, conditions for easily distinguishing live cells of microorganism from dead or injured cells of microorganism can be determined by: adding various concentrations of a cross-linker to suspensions of live cells of microorganism to be detected and dead or injured cells of microorganism; allowing the suspensions to stand for various periods of time; separating the cells by centrifugation; and analyzing the cells by the nucleic acid amplification method. Moreover, conditions for easily distinguishing live cells of microorganism from various cells can be determined by: adding various concentrations of a cross-linker to suspensions of live cells of microorganism to be detected and somatic cells such as bovine leukocytes or thrombocytes; allowing the suspensions to stand for various periods of time; separating the cells and the various cells by centrifugation; and analyzing the cells by the nucleic acid amplification method. Specifically: conditions of a treatment with ethidium monoazide at a final concentration of 1 to 100 µg/ml for 5 minutes to 48 hours at 4 to 10° C.; conditions of a treatment with ethidium diazide at a final concentration of 1 to 100 µg/ml for 5 minutes to 48 hours at 4 to 10° C.; conditions of a treatment with psolaren at a final concentration of $1 \times 10^{-5}$ to 10 µg/ml for 5 minutes to 48 hours at 25 to 37° C.; conditions of a treatment with 4,5',8-trimethyl psolaren at a final concentration of $1 \times 10^{-5}$ to 10 µg/ml for 5 minutes to 48 hours at 25 to 37° C.; and conditions of a treatment with 8-methoxy psolaren at a final concentration of $1 \times 10^{-5}$ to 10 µg/ml for 5 minutes to 48 hours at 25 to 37° C. are exemplified.

(2) Step b)

Next, each test sample containing the cross-linker is irradiated with light having a wavelength of 350 nm to 700 nm.

The cross-linker can easily pass through cell walls of dead cells and injured cells compared with cell walls of live cells of microorganism. Therefore, it is presumed that the cross-linker does not substantially pass through cell walls of live cells of microorganism but passes through cell walls of injured or dead cells of microorganism, or dead somatic cells, provided that the treatment is performed within the above-mentioned periods of time. Meanwhile, live somatic cells have only cell membranes and no cell walls, and hence it is presumed that the cross-linker passes through the somatic cells. As a result, the cross-linker moves into dead somatic cells, dead and injured cells of microorganism, and randomly binds by covalent attachment to or intercalates into chromosomal DNA. Subsequently, the cross-linker is irradiated with light having a wavelength of 350 nm to 700 nm to cross-link DNA molecules and causes a large deformation in the chromosomal DNA, resulting in disrupting (fragmentating/cleaving) the chromosomal DNA.

The light having a wavelength of 350 nm to 700 nm may include at least light having a wavelength of 350 nm to 700 nm, and the light may be single-wavelength light or multi-wavelength light. In addition, all light components may be in the range of 350 nm to 700 nm, or the light may include short-wavelength light having a wavelength shorter than 350 nm and/or long-wavelength light having a wavelength longer than 700 nm. The peak in an intensity distribution is preferably in the range of 350 nm to 700 nm. Preferably, the light does not include a component with a short wavelength to such a degree that chromosomal DNA of a microorganism is cleaved only by light irradiation.

When chromosomal DNA of injured or dead cells is more preferentially disrupted than that of live cells of microorganism, a target region of the chromosomal DNA of the live cells is amplified by the nucleic acid amplification method, while a target region of the injured or dead cells is disrupted (cleaved), resulting in inhibiting the nucleic acid amplification reactions. As a result, the live cells of microorganism can be detected more selectively than the injured or dead cells.

In a preferred embodiment of the present invention, the cross-linker is ethidium monoazide, and the method includes the step of irradiating a test sample to which ethidium monoazide is added with light having a wavelength of 350 nm to 700 nm. Ethidium monoazide (EMA) can easily pass through cell walls of injured or dead cells compared with cell walls of live cells of microorganism. Therefore, it is presumed that EMA does not substantially pass through cell walls of live cells of microorganism but passes through cell walls of injured or dead cells of microorganism or cell membranes of dead somatic cells. Note that, in the case where leukocytes and thrombocytes in blood are live cells, EMA can more easily pass through cell walls of the cells in sterilized water or a hypotonic salt solution. EMA moves into dead somatic cells and injured and dead cells and intercalates randomly into nuclear DNA, and only EMA intercalated by irradiation with light having a wavelength of 350 nm to 700 nm is converted into nitrene and binds covalently to nuclear DNA to cross-link DNA molecules. Then, it is presumed that EMA which binds covalently to bases and deoxyriboses in chromosomal DNA at many points causes a large deformation in the chromosomal DNA, resulting in disrupting (fragmentating) the chromosomal DNA.

Even if the cross-linker is other than ethidium monoazide, a cross-linker may be used in the present invention as long as the cross-linker can more easily pass through cell walls of injured or dead cells compared with cell walls of live cells of microorganism and can cross-link DNA by irradiation with light having a wavelength of 350 nm to 700 nm (long-wavelength ultraviolet light or visible light) to thereby disrupt chromosomal DNA.

Conditions for the treatment with EMA can be appropriately determined. For example, conditions that enables easy distinction of live cells of microorganism from dead cells and injured cells can be determined by adding EMA at various concentrations to suspensions of live cells and injured cells or dead cells of the microorganism as an object of detection, leaving them for various periods of time, then irradiating them with visible light, removing the cells by centrifugation or the like as required, and performing analysis by nucleic acid amplification methods. Preferred conditions for the irradiation of visible light can also be appropriately determined by performing such an experiment as mentioned above using various irradiation times. Specific examples of the conditions for the irradiation of visible light include irradiation of visible lights of 100 to 750 W for 5 minutes to 2 hours from a distance of 10 to 50 cm from the test sample. The irradiation of visible light is preferably performed at a low temperature, for example, with ice cooling of the sample.

(3) Step c)

An unreacted cross-linker contained in the test sample treated by light irradiation is removed from the test sample.

This step is preferably performed immediately after step b). Examples of the method of removing a cross-linker include a method involving: centrifuging the test sample to separate precipitates containing microorganisms from supernatant containing the cross-linker; and removing the supernatant. The method may further include, after removing the cross-linker, a step of washing the microorganisms with a cleaning agent.

(4) Step d)

Subsequently, a medium is added to the test sample where the cross-linker is removed, and the resultant is incubated.

The medium is preferably one suitable for culture of a microorganism contained in the test sample, and a liquid medium is particularly preferably used. Specific examples thereof include bouillon medium, peptone medium, and brain heart infusion (BHI) broth. Incubation is preferably performed at a temperature suitable for proliferation of a microorganism to be detected, for example, at an optimum culture temperature of the microorganism or at a temperature similar to the optimum culture temperature. The optimum culture temperature of the microorganism may be determined by: culturing the microorganism at various temperatures; and selecting a temperature where the microorganism can proliferate most actively. For example, in the cases of the above-mentioned bacteria, the temperature is usually 20° C. to 43° C., preferably 25° C. to 37° C., more preferably 30° C. to 37° C. The incubation time is not particularly limited as long as a microorganism in a sample can proliferate. Specifically, the time is, for example, 0.5 to 48 hours, preferably 1 to 24 hours, more preferably 2 to 3 hours. When a test sample containing a microorganism is incubated in a medium, live cells of microorganism having no cross-linker and having no disrupted chromosomal DNA can proliferate by culture with incubation in the medium, which may improve the detection sensitivity in discrimination between presence and absence of live cells of microorganism in the test sample and in determination of the amount of the live cells of microorganism.

(5) Steps e) and f)

Steps e) and f) are performed in the same way as in steps a) and b), respectively.

It is expected that live cells of microorganism in a test sample are proliferated by performing step d), so it is possible to increase a difference between the detection sensitivity of live cells and the detection sensitivity of the other cells by performing steps e) and f) after step d). This can drastically improve the detection sensitivity in discrimination between presence and absence of live, injured, or dead cells in the test sample and in determination of the amount of live cells of microorganism. The cross-linker added in step e) and the cross-linker added in step a) may be the same or different from each other.

The particularly preferred aspect of the present invention is to sequentially perform: addition of a cross-linker to a test sample and a light irradiation treatment; removal of the cross-linker by centrifugation; addition and incubation of a medium; further addition of the cross-linker and a light irradiation treatment. After the above-mentioned sequential treatments, the following process may be repeated several times to further improve the detection sensitivity: removal of the cross-linker; addition and incubation of the medium; and further addition of the cross-linker and a light irradiation treatment. Specifically, steps c), d), e), and f) may be repeated twice or more after steps a) and b).

In Examples and Comparative Examples below, a process which includes only steps a) and b) and does not include steps e) and f) is sometimes referred to as "single-step treatment", while a process which includes not only steps a) and b) but also steps e) and f) is sometimes referred to as "multi-step treatment".

(6) Step g)

DNA is extracted from each of the test samples treated in steps a to f) and a target region of the extracted DNA is amplified by a nucleic acid amplification method. Examples of the nucleic acid amplification method include PCR method (White, T. J. et al., Trends Genet., 5, 185 (1989)), LAMP method (Loop-Mediated Isothermal Amplification: principal and application of novel gene amplification method (LAMP method), Tsugunori Notomi, Toru Nagatani, BIO INDUSTRY, Vol. 18, No. 2, 15-23, 2001), SDA method (Strand Displacement Amplification: Edward L. Chan, Ken Brandt, Karen Olienus, Nick Antonishyn, Greg B. Horsman., Performance characteristics of the Becton Dickinson ProbeTec System for direct detection of *Chlamydia trachomatis* and *Neisseria gonorrhoeae* in male and female urine specimens in comparison with the Roche Cobas system. Arch. Pathol. Lab. Med., 124:1649-1652, 2000), LCR method (Ligase Chain Reaction: Barany, F., Proc. Natl. Acad. Sci. USA, Vol. 88, p. 189-193, 1991), DNA microarray method (Validation of Virulence and Epidemiology DNA Microarray for Identification and Characterization of *Staphylococcus aureus* Isolates: Richard P. Spence, et al., J. Clin. Microbiol., Vol. 46, No. 5, p. 1620-1627, 2008). In the present invention, the PCR method is particularly preferably used, the nucleic acid amplification method is not limited thereto.

The method for extracting DNA from the test sample is not particularly limited so long as the extracted DNA can function as a template in PCR, and the extraction can be performed according to a commonly used method for extracting DNA of a microorganism.

The DNA extraction method is described in, for example, Maniatis T. and Fritsch E. F., Sambrook, J., "Molecular Cloning: A Laboratory Manual", 3rd edn., Cold Spring Harbor, N.Y.: Cold Spring Harbor Laboratory Press, 2001.

In the present invention, the "target region" is not particularly limited so long as a region of a chromosomal DNA that can be amplified by PCR using primers used for the present invention and enables detection of a microorganism to be detected is chosen, and it can be suitably chosen depending on the purpose. For example, when cells of a type different from that of the microorganism to be detected are contained in the test sample, the target region preferably contains a sequence specific to the microorganism as an object of the detection. Further, depending on the purpose, the target region may be one containing a sequence common to several kinds of microorganisms. Furthermore, the target region may consist of a single region or two or more regions. If a primer set suitable for a target region specific to the microorganism as an object of the detection and a primer set suitable for chromosomal DNAs of wide varieties of microorganisms are used, live cell amount of the microorganism as the object of the detection and live cell amount of the wide varieties of microorganisms can be simultaneously measured. Length of the target region is, for example, usually 50 to 5000 nucleotides, preferably 50 to 2000 nucleotides, particularly preferably 50 to 500 nucleotides.

The primers to be used in amplification of a nucleic acid may be selected based on principles of various nucleic acid amplification methods and are not particularly limited as long as the primers can specifically amplify the above-mentioned target region.

In the case where the microorganism of the detection target is a pathogenic bacterium, the target region may be a pathogenic gene. Examples of the pathogenic gene include: listeriolysin O (hlyA) gene of a *Listeria* bacterium; enterotoxin gene and invasion (invA) gene of a *Salmonella* bacterium; verotoxin gene of pathogenic *Escherichia coli* O-157; outer-membrane-protein A (ompA) gene (*Enterobacter sakazakii*) and macromolecular synthesis (MMS) operon (*Enterobacter sakazakii*) of an *Enterobacter* bacterium; enterotoxin gene of *Staphylococcus aureus*; cereulide gene and enterotoxin gene of *Bacillus cereus*; and various toxin genes of *Clostridium botulinum*. Examples of primers for a pathogenic gene include: a set of primers represented by SEQ ID NOS: 1 and 2 for hlyA gene of *Listeria*; a set of primers represented by SEQ ID NOS: 3 and 4 for ompA gene of *Enterobacter sakazakii*; and a set of primers represented by SEQ ID NOS: 5 and 6 for MMS operon of *Enterobacter sakazakii*.

If primers suitable for two or more kinds of microorganisms are used, live cells of two or more kinds of the microorganisms in a test sample can be detected. Moreover, if a primer (s) specific to a particular bacterium are used, live cell of the particular bacterium in a test sample can be detected.

Conditions of nucleic acid amplification reactions are not particularly limited as long as a nucleic acid can be specifically amplified based on principles of various nucleic acid amplification methods (such as PCR, LAMP, SDA, and LCR), and the conditions may be appropriately set.

(7) Step h)

Subsequently, amplified products obtained by the nucleic acid amplification method are analyzed.

The analysis method is not particularly limited as long as the method can detect or quantify the nucleic acid amplified products, and examples thereof include electrophoresis. Note that, in the case of using PCR method for the nucleic acid amplification method, a real-time PCR method can be used (Nogva et al./Application of 5'-nuclease PCR for quantitative detection of *Listeria monocytogenes* in pure cultures, water, skim milk, and unpasteurized whole milk. Appl. Environ. Microbiol., vol. 66, 2000, pp. 4266-4271, Nogva et al./Application of the 5'-nuclease PCR assay in evaluation and development of methods for quantitative detection of *campylobacter jejuni*. Appl. Environ. Microbiol., vol. 66, 2000, pp. 4029-4036).

The electrophoresis is employed for evaluation of the amounts and sizes of the nucleic acid amplified products. In addition, real-time PCR is employed for rapid quantification of PCR amplified products.

In the case where the real-time PCR is employed, changes in fluorescent intensities are generally noise levels and about zero if the number of amplification cycles is in the range of 1 to 10. Therefore, the intensities are regarded as sample blanks containing no amplification products. The standard deviation (SD) of the changes is calculated, and a value obtained by multiplying the SD value by 10 is defined as a threshold value. The number of PCR cycles in which a value larger than the threshold value is achieved for the first time referred to as "cycle threshold value (Ct value)". Therefore, the larger the initial amount of a DNA template in a PCR reaction solution, the smaller the Ct value, while the smaller the amount of the template DNA, the larger the Ct value. Even if the amounts of the template DNA are the same, the higher the proportion of the template where a target region of PCR has been cleaved, the larger the Ct value in PCR reactions for the region.

Further, presence or absence of the amplification product can also be determined by analyzing the melting temperature (TM) pattern of the amplification product.

All the aforementioned methods can also be used for optimization of various conditions for the method of the present invention.

When live cells of microorganism are detected by the method of the present invention, precisions of the determination of the presence or absence of live cells of microorganism and quantification of the same in the analysis of the PCR amplification product can be increased by using a standard curve representing relationship between the amount of microorganism and the amplification product, which is prepared by using standard samples of the microorganism in which the microorganism is identified. Although a preliminarily prepared standard curve may be used, it is preferable to use a standard curve prepared by performing the steps of the method of the present invention for standard samples at the same time with a test sample. Moreover, if relationship between amount of microorganism and amount of DNA is determined beforehand, DNA isolated from the microorganism can also be used as a standard sample.

In the case where detection of live cells of microorganism by the present invention includes determination of the amount of the live cells of microorganism, in order to determine the amount of the live cells of microorganism in a test sample, it is necessary to consider the proliferation degree of the live cells of microorganism because the live cells of microorganism proliferate in step d). This can be achieved by creating a standard curve showing the relationship between the amount of microorganism and amplified products using a standard sample of the microorganism, as described above.

<2> Kit of the Present Invention

The kit of the present invention is a kit for detecting live cells of microorganism in a test sample by the nucleic acid amplification method and comprises a cross-linker, a medium, and a primer (s) for amplifying a target region of DNA of a microorganism to be detected by the nucleic acid amplification method.

The nucleic acid amplification reaction is preferably a PCR, LAMP, SDA, or LCR. The cross-linker and medium are the same as described in the method of the present invention.

In the kit, according to a preferred aspect of the present invention, the cross-linker is selected from ethidium monoazide, ethidium diazide, psolaren, 4,5',8-trimethyl psolaren, and 8-methoxy psolaren. Ethidium monoazide is particularly preferably used.

The kit of the present invention may further comprise a diluting solution, a reaction solution for cross-linker reaction, and an instruction describing the method of the present invention.

EXAMPLES

Hereinafter, the present invention is described more specifically with reference to the following examples. However, the present invention is not limited to the examples.

Example 1

1. Preparation of sample—Preparation of *Listeria monocytogenes* (live cell and injured cell) suspensions A Gram-positive bacterium, *Listeria monocytogenes* (*Listeria monocytogenes* JCM 2873; hereinafter, abbreviated as "*Listeria*" in some cases), was cultured in brain-heart infusion (BHI) broth at 30° C., and 40 ml of the culture medium in the logarithmic growth phase was centrifuged at 8,000×g for 15 minutes at 4° C., followed by removal of the supernatant. 40 ml of physiological saline was added to the bacterial cells, and the whole was vigorously stirred and centrifuged in the same way as above. The supernatant was removed, and 10 ml of physiological saline was added to the bacterial cells, to thereby prepare a live cell suspension. The number of the live cells in the live cell suspension was determined in a standard agar plate medium and found to be $1.3 \times 10^8$ cfu/ml.

The live cell suspension (1 ml) was placed in a 1.5-ml microtube, and the microtube was immersed in boiling water for 50 seconds and immediately cooled with ice water, to thereby prepare a injured cell suspension. The cells in the suspension probably include small numbers of live cells and dead cells but include mainly injured cells. Therefore, the cells are simply referred to as "injured cells". The method of the present invention is originally intended to detect live cells of microorganism, and cells of microorganism distinguished from live cells may be injured cells or dead cells.

2. Test Method 2-1) Multi-Step Treatment (Method of the Present Invention)

Ethidium monoazide (EMA) was added to the live cell suspension and injured cell suspension of *Listeria* prepared above at a final concentration of 0 or 100 µg/ml, and the suspensions were allowed to stand under shading at 4° C. for 5 minutes. The suspensions were placed on ice and irradiated for 5 minutes with a 500-W visible light (FLOOD PRF: 100 V, 500 W, IWASAKI ELECTRIC CO., LTD., wavelength: 500 to 700 nm) at a distance of 20 cm from the suspensions. Then, the suspensions were centrifuged at 15,000×g for 10 minutes at 4° C., and the supernatants were removed. An equal volume of physiological saline was added thereto, and the suspensions were stirred and centrifuged while cooling at 15,000×g for 10 minutes at 4° C., followed by removal of the supernatants. An equal volume of brain-heart infusion (BHI) broth was added thereto, and the suspensions were incubated at 30° C. for 2 hours.

In the first EMA treatment, EMA was not added again to the live cell and injured cell suspensions having an EMA concentration of 0, while EMA was added again at a final EMA concentration of 10 µg/ml or 25 µg/ml to the live cell and injured cell suspensions having an EMA concentration of 100 µg/ml. The suspensions were allowed to stand under shading at 4° C. for 5 minutes, placed on ice, and irradiated for 5 minutes with a 500-W visible light at a distance of 20 cm from the suspensions.

2-2) Single Treatment (Comparative Example 1)

Ethidium monoazide (EMA) was added to the live cell and injured cell suspensions of *Listeria* prepared in the section "1." at a final concentration of 0, 10, or 25 µg/ml, and the suspensions were allowed to stand under shading at 4° C. for 5 minutes, placed on ice, and irradiated for 5 minutes with a 500-W visible light (FLOOD PRF: 100V, 500 W, IWASAKI ELECTRIC CO., LTD., wavelength: 500 to 700 nm) at a distance of 20 cm from the suspensions.

2-3) Preparation of Bacterium Suspension to be Used in PCR Test

Microtubes including one of the live cell and injured cell suspensions of *Listeria* treated in the sections 2-1) and 2-2) above were centrifuged at 15,000×g for 10 minutes at 4° C. The supernatants were removed, and 1 ml of physiological saline was added thereto. The resultant suspensions were stirred vigorously and centrifuged in the same way as above (washing treatment). One more washing treatment was performed in the same way as the first treatment, and 10 µl of TE buffer (10 mM Tris-HCl buffer, 1 mM EDTA·2Na) was added to the pellets, followed by vigorous stirring.

3. PCR Targeting Pathogenic Gene (Short DNA) of *Listeria*

3-1) Amplification of Pathogenic Gene, *Listeria listeriolysin* O (hlyA) Gene

PCR Master Mix (total volume: 50.5 µl) was prepared using Direct Buffer Mix (G&g SCIENCE CO., LTD., Yokohama, Kanagawa) capable of sequentially and automatically performing elution of chromosomal DNA from a bacterium and PCR reactions. The Buffer Mix contains: a component (surfactant) for inhibiting adsorption of a protein derived from a bacterium to a template DNA derived from a bacterium to be used in PCR reactions; and a component (surfactant) for inhibiting adsorption of a polysaccharide derived from a bacterium to a DNA polymerase; and further an ingredient necessary for real-time PCR reactions. Details of the PCR Master Mix are as follows.

Direct buffer MIX manufactured by G&g SCIENCE. CO., LTD.: 42 µl (5 U/µl) Ex-Taq (manufactured by TAKARA SHUZO CO., LTD, catalog No: RR001B): 0.5 µl (10 pmol/µl) SEQ ID NO: 1 (hlyA-F) DNA: 4 µl (10 pmol/µl) SEQ ID NO: 2 (hlyA-R) DNA: 4 µl Note that, the total amount of the above-mentioned reagents is 50.5 µl and in Direct buffer MIX manufactured by G&g SCIENCE. CO., LTD., required components for PCR Master Mix in total amount of 50.5 µl have been prepared to have the following final concentrations beforehand.

Ex-Taq Buffer (TAKARA SHUZO CO., LTD, catalog No: RR001B): 1× dNTP mixture (TAKARA SHUZO CO., LTD, catalog No: RR001B): 0.2 mM each

SYBA Green (manufactured by BMA, catalog No: 50513): 0.4×

3-2) Thermal Cycle Profile of PCR for Amplification of hlyA Gene

TABLE 1

Thermal cycle profile of PCR for amplification of hlyA gene

| Cycle | Repeats | Step | Retention time | Hold | Set (° C.) | Temperature rising gradient (° C.) |
|---|---|---|---|---|---|---|
| 1 | 1 | 1 | 03:00 | | 4 | |
| 2 | 1 | 1 | 00:30 | | 94 | |
| 3 | 50 | 1 | 00:20 | | 95 | |
| | | 2 | 01:00 | | 60 | |
| 4 | 1 | 1 | 03:00 | | 95 | |
| 5 | 350 | 1 | 00:08 | | 60 | 0.1 |
| 6 | | | | ∞ | 4 | |

3-3) PCR Reaction

The test suspensions prepared in the section 2-3) above (5 µl each) were added to the PCR Master Mix (50.5 µl) prepared in the section 3-1) above. TE buffer (5 µl) was used as a negative control.

According to the PCR thermal cycle profile shown in the section 3-2), PCR reactions were performed using a real-time PCR device (iCycler, manufactured by Bio-Rad Laboratories, Inc., Model: iQ).

4. Agarose Gel Electrophoresis for PCR Amplified Product

The PCR amplified products obtained in the section 3-3) above were electrophoresed on a 3% agarose gel. After completion of the electrophoresis, the agarose gel was immersed in an aqueous solution of 1 µg/ml ethidium bromide for 20 minutes and washed twice with ion-exchange water, and a UV transilluminator (wavelength: 254 nm) was used to observe the amplification degrees of the hlyA gene amplified products.

5. Test Results

FIG. 1 shows the results obtained by performing: the multi-step treatment for the live cells and injured cells of *Listeria*; PCR for the hlyA gene; and agarose gel electrophoresis (multi-step treatment lane), while Table 2 shows data obtained by quantifying band intensities of the final PCR amplified products. Meanwhile, FIG. 1 shows the results obtained by performing: the single-step treatment for the live cells and injured cells of *Listeria*; PCR for the hlyA gene; and agarose gel electrophoresis (single-step treatment lane), and Table 3 shows data obtained by quantifying band intensities of the final PCR amplified products. The band intensities in the tables are values measured by scanning the color strength of each band in the electrophoresis direction using GS-700 Imaging Densitometer manufactured by Bio-Rad Laboratories, Inc. (densitometer: measurement wavelength 600 nm).

TABLE 2

| | EMA 0 µg/ml + Incubation (30° C., 2 hr) + EMA 0 µg/ml | | EMA 100 µg/ml + Incubation (30° C., 2 hr) + EMA 10 µg/ml | | EMA 100 µg/ml + Incubation (30° C., 2 hr) + EMA 25 µg/ml | |
|---|---|---|---|---|---|---|
| | Live cell | Injured cell | Live cell | Injured cell | Live cell | Injured cell |
| Band Intensity | 1.637 | 1.431 | 1.420 | 0.094 | 1.135 | 0.024 |

TABLE 3

| | EMA 0 µg/ml | | EMA 10 µg/ml | | EMA 25 µg/ml | |
|---|---|---|---|---|---|---|
| | Live cell | Injured cell | Live cell | Injured cell | Live cell | Injured cell |
| Band Intensity | 1.695 | 1.215 | 1.141 | 1.539 | 0.479 | 0.418 |

In the case where EMA was not added in the multi-step treatment, bands which were estimated as hlyA gene amplified products were detected in both the live cells and injured cells of *Listeria*, and it was impossible to specifically detect only live cells. However, in the case where EMA was added in the multi-step treatment (EMA 100 µg/ml-incubation-EMA 25 or 10 µg/ml), bands were clearly detected in the live cells, while few or no bands were detected in the injured cells. The results suggest that the multi-step treatment enables selective detection of only the live cells in PCR. As is obvious from the data obtained by quantifying the band intensities (shown in Table 2), the multi-step treatment enabled clear discrimination of the live cells from injured cells in PCR targeting the short gene (113 bp).

On the other hand, in the case where EMA was not added in the single-step treatment, bands estimated as hlyA gene amplified products were detected by PCR in both the live cells and injured cells of *Listeria*, and it was impossible to selectively detect only the live cells. Meanwhile, in the case where EMA was added at a concentration of 10 µg/ml in the single-step treatment, bands estimated as hlyA gene amplified products were detected in both the live cells and injured cells, and it was impossible to specifically detect only the live cells. In the case where EMA was added at a concentration of 25 µg/ml in the single-step treatment, bands estimated as hlyA gene amplified products almost disappeared in both the live cells and injured cells, and it was impossible to specifically detect only the live cells. As shown in Table 3, the single-step treatment could not achieve clear discrimination of the live cells from injured cells in PCR targeting as short gene as hlyA (113 bp).

6. Discussion

In the case where live cells are rapidly distinguished from injured cells (including dead cells) while focusing on a specific pathogenic bacterium, a short gene region with a size of 80 to 200 bases may be targeted to detect specifically only the pathogenic bacterium and to quantify the number of bacterial cells in a test sample by quantitative real-time PCR. In the case where a sample is treated with EMA at a concentration of higher than 10 µg/ml by the single-step treatment as shown in Comparative Example 1, EMA passes through not only cell walls of injured cells but also cell walls of live cells to directly cleave double strands of chromosomal DNA of the live and injured cells at many points independently of enzymes in the bacterium. Therefore, it is impossible to specifically detect only the live cells. Meanwhile, in the case where a sample is treated with EMA at a concentration equal to or less than 10 µg/ml by the single-step treatment, EMA is hard to pass through cell walls of injured cells, and chromosomal DNA is unlikely to be cleaved frequently. Therefore, in the case where the PCR target region is short, the target regions of chromosomal DNAs of all injured cells are not always cleaved, and hence, PCR is not completely inhibited.

On the other hand, after EMA is added once in the multi-step treatment, even if part of EMA passes through live cells to reduce the number of live cells, it is possible to recover the number of live cells to the initial value, to recover a diffusion pump of the live cells, or to remove unreacted EMA to the outside of the microorganism cells by incubation in a medium suitable for culture. Therefore, the concentration of EMA to be added in the first treatment may be high (for example, 100 μg/ml), and chromosomal DNA of injured cells is cleaved with a high concentration of EMA at many points. Even if the injured cells are incubated in the medium, it is impossible to increase the number of the cells unlike live cells. Under such circumstances, if EMA is added again at a certain concentration (for example, 10 μg/ml) where little EMA passes through cell walls of live cells in a short time (for example, 5 minutes), EMA passes through only cell walls of injured cells to promote further cleavage of chromosomal DNA, and bands of final PCR amplified products may not be detected only in the case of injured cells.

Example 2

1. Preparation of Sample—Preparation of *Enterobacter sakazakii* (Live Cell and Injured Cell) Suspensions A Gram-negative bacterium, *Enterobacter sakazakii* (*Enterobacter sakazakii* ATCC 6538P; hereinafter, abbreviated as "*sakazakii*" in some cases), was cultured in brain-heart infusion (BHI) broth at 37° C., and 5 ml of the culture medium in the logarithmic growth phase was centrifuged at 8,000×g for 15 minutes at 4° C., followed by removal of the supernatant. 5 ml of physiological saline was added to the bacterial cells, and the whole was vigorously stirred and diluted 10-fold. Thus, a live cell suspension was prepared. The number of the live cells in the live cell suspension was determined in a standard agar plate medium and found to be 8.38±0.25 $\log_{10}$ cfu/ml.

The live cell suspension (1 ml) was placed in a 1.5-ml microtube, and the microtube was immersed in boiling water for 2 minutes and immediately cooled with ice water, to thereby prepare a injured cell suspension. The cells in the suspension probably include small numbers of live cells and dead cells but include mainly injured cells. Therefore, the cells are simply referred to as "injured cells". Note that the method of the present invention is originally intended to detect live cells, and microorganism cells distinguished from live cells may be injured cells or dead cells.

2. Test Method 2-1) Multi-Step Treatment (Method of the Present Invention)

Ethidium monoazide (EMA) was added to the live cell suspension and injured cell suspension of *sakazakii* prepared above at a final concentration of 0, 10, 25, or 100 μg/ml, and the suspensions were allowed to stand under shading at 4° C. for 10 minutes. The suspensions were placed on ice and irradiated for 5 minutes with a 500-W visible light (FLOOD PRF: 100V, 500 W, IWASAKI ELECTRIC CO., LTD., wavelength: 500 to 700 nm) at a distance of 20 cm from the suspensions. Then, the suspensions were centrifuged at 15,000×g for 10 minutes at 4° C., and the supernatants were removed. An equal volume of physiological saline was added thereto, and the suspensions were stirred and centrifuged while cooling at 15,000×g for 10 minutes at 4° C., followed by removal of the supernatants. An equal volume of brain-heart infusion (BHI) broth was added thereto, and the suspensions were incubated at 37° C. for 2 hours.

In the first EMA treatment, EMA was not added again to the live cell and injured cell suspensions having an EMA concentration of 0, while EMA was added again at a final concentration of 10 μg/ml to the live cell and injured cell suspensions having an EMA concentration of 10, 25, or 100 μg/ml. The suspensions were allowed to stand under shading at 4° C. for 10 minutes, placed on ice, and irradiated for 5 minutes with a 500-W visible light at a distance of 20 cm from the suspensions.

2-2) Single Treatment (Comparative Example 2)

Ethidium monoazide (EMA) was added to the live cell and injured cell suspensions of *sakazakii* prepared in the section "1." at a final concentration of 0, 10, 25 or 100 μg/ml, and the suspensions were allowed to stand under shading at 4° C. for 10 minutes, placed on ice, and irradiated for 5 minutes with a 500-W visible light (FLOOD PRF: 100V, 500 W, IWASAKI ELECTRIC CO., LTD., wavelength: 500 to 700 nm) at a distance of 20 cm from the suspensions.

2-3) Preparation of Bacterium Suspension to be Used in PCR Test

Microtubes including one of the live cell and injured cell suspensions of *sakazakii* treated in the sections 2-1) and 2-2) above were centrifuged at 15,000×g for 10 minutes at 4° C. The supernatants were removed, and 1 ml of physiological saline was added thereto. The resultant suspensions were stirred vigorously and centrifuged while cooling in the same way as above (washing treatment). One more washing treatment was performed in the same way, and the same amount of sterile water as the initial amount was added to the pellets, followed by vigorous stirring.

3. PCR Targeting Outer-Membrane-Protein A (omp A) Gene and Macromolecular Snthesis (MMS) Operon (short DNA) of *Sakazakii*

3-1) Amplification of omp A Gene and MMS Gene

PCR Master Mix (total volume: 25.25 μl) was prepared using Direct Buffer Mix (G&g SCIENCE CO., LTD., Yokohama, Kanagawa) capable of sequentially and automatically performing elution of chromosomal DNA from a bacterium and PCR reactions. The Buffer Mix contains: a component (surfactant) for inhibiting adsorption of a protein derived from a bacterium to a template DNA derived from a bacterium to be used in PCR reactions; and a component (surfactant) for inhibiting adsorption of a polysaccharide derived from a bacterium to a DNA polymerase; and further an ingredient necessary for real-time PCR reactions. Details of the PCR Master Mix are as follows.

Each component of PCR Master Mix for detecting ompA gene is as follows.
Direct buffer MIX manufactured by G&g SCIENCE. CO., LTD.: 21 μl
(5 U/μl) Ex-Taq (manufactured by TAKARA SHUZO CO., LTD, catalog No: RR001B): 0.25 μl
(10 pmol/μl) SEQ ID No: 3 (ompA-F) DNA: 2 μl
(10 pmol/μl) SEQ ID No: 4 (ompA-R) DNA: 2 μl Each component of PCR Master Mix for detecting MMS gene is as follows.
Direct buffer MIX manufactured by G&g SCIENCE. CO., LTD.: 21 μl
(5 U/μl) Ex-Taq (manufactured by TAKARA SHUZO CO., LTD, catalog No: RR001B): 0.25 μl
(10 pmol/μl) SEQ ID NO: 5 (MMS-F) DNA: 2 μl
(10 pmol/μl) SEQ ID NO: 6 (MMS-R) DNA: 2 μl Note that, the total amount of the above-mentioned reagents is 25.25 μl and in Direct buffer MIX manufactured by G&g SCIENCE. CO., LTD., required components in PCR Master Mix of total amount of 25.25 μl have been prepared to have the following final concentrations beforehand.
Ex-Taq Buffer (manufactured by TAKARA SHUZO CO., LTD, catalog No: RR001B): 1×
dNTP mixture (manufactured by TAKARA SHUZO CO., LTD, catalog No: RR001B): 0.2 mM each
SYBA Green (manufactured by BMA, catalog No: 50513): 0.4×

3-2) Thermal Cycle Profile of PCR for Amplification of ompA Gene and MMS Gene

TABLE 4

Thermal cycle profile of PCR for amplification of ompA gene and MMS gene

| Cycle | Repeats | Step | Retention time | Hold | Set (° C.) | Temperature rising gradient (° C.) |
|---|---|---|---|---|---|---|
| 1 | 1 | 1 | 03:00 | | 4 | |
| 2 | 1 | 1 | 02:00 | | 94 | |
| 3 | 50 | 1 | 00:30 | | 94 | |
| | | 2 | 00:40 | | 60 | |
| | | 3 | 00:45 | | 68 | |
| 4 | 1 | 1 | 03:00 | | 95 | |
| 5 | 250 | 1 | 00:08 | | 70 | 0.1 |
| 6 | | | | ∞ | 4 | |

3-3) PCR Reaction

The test suspensions prepared in the section 2-3) above (2 μl each) were added to the PCR Master Mix (25.25 μl) prepared in the section 3-1) above. Sterile water (2.5 μl) was used as a negative control.

According to the PCR thermal cycle profile shown in the section 3-2), PCR reactions were performed using a real-time PCR device (iCycler, Bio-Rad Laboratories, Inc., Model: iQ).

4. Agarose Gel Electrophoresis for PCR Amplified Product

The PCR amplified products obtained in the section 3-3) above were electrophoresed on a 2% agarose gel. After completion of the electrophoresis, the agarose gel was immersed in an aqueous solution of 1 μg/ml ethidium bromide for 20 minutes and washed twice with ion-exchange water, and a LTV transilluminator (wavelength: 254 nm) was used to observe the amplification degrees of the ompA gene and MMS gene amplified products.

5. Test Results

Figure 2:
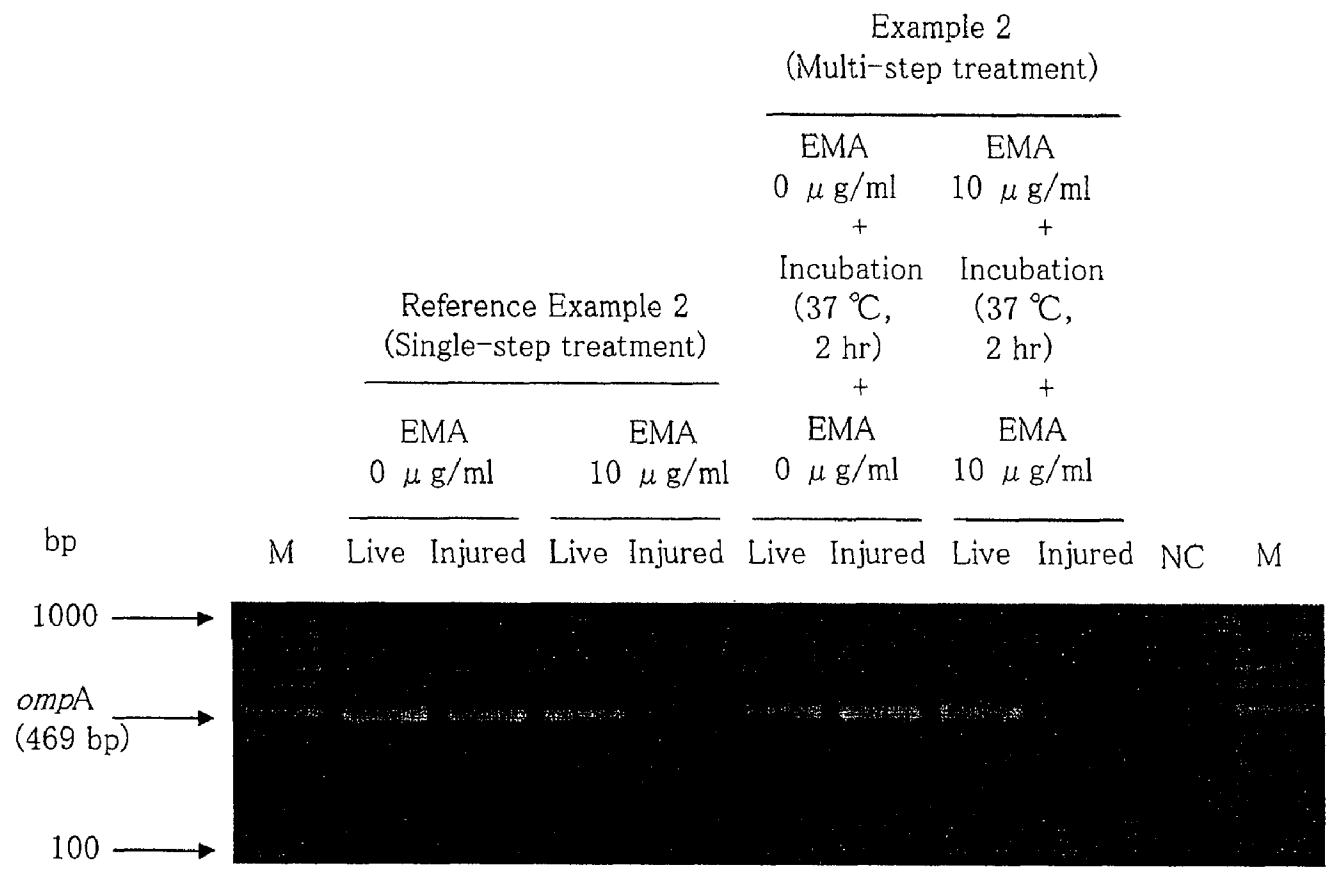

FIG. 2 shows the results obtained by performing: the multi-step treatment for the live cells and injured cells of *sakazakii*; PCR for the ompA gene; and agarose gel electrophoresis (multi-step treatment lane), while Table 5 shows data obtained by quantifying band intensities of the final PCR amplified products. Meanwhile, FIG. 2 shows the results obtained by performing: the single-step treatment for the live cells and injured cells of *sakazakii*; PCR for the ompA gene; and agarose gel electrophoresis (single-step treatment lane), and Table 6 shows data obtained by quantifying band intensities of the final PCR amplified products. The band intensities in the tables are values measured by scanning the color strength of each band in the electrophoresis direction using GS-700 Imaging Densitometer manufactured by Bio-Rad Laboratories, Inc. (densitometer: measurement wavelength 600 nm). Moreover, Table 7 shows the number of cycles at initial rising in each real-time PCR curve in the multi-step treatment or single-step treatment (Ct value).

FIG. 3 shows the results of the electrophoresis for final PCR amplified products of the MMS gene after the multi-step treatment (multi-step treatment lane), and Table 8 shows data obtained by quantifying the PCR bands. Meanwhile, FIG. 3 shows the results of the electrophoresis after the single-step treatment (single-step treatment lane), and Table 9 shows data obtained by quantifying the PCR bands. Meanwhile, Table 10 shows the number of cycles at initial rising in each real-time PCR curve in the multi-step treatment or single-step treatment (Ct value).

TABLE 5

| | EMA 0 μg/ml + Incubation (37° C., 2 hr) + EMA 0 μg/ml | | EMA 10 μg/ml + Incubation (37° C., 2 hr) + EMA 10 μg/ml | |
|---|---|---|---|---|
| | Live cell | Injured cell | Live cell | Injured cell |
| Band Intensity | 1.514 | 1.681 | 1.546 | 0.000 |

TABLE 6

| | EMA 0 μg/ml | | EMA 10 μg/ml | |
|---|---|---|---|---|
| | Live cell | Injured cell | Live cell | Injured cell |
| Band Intensity | 1.551 | 1.556 | 1.690 | 0.502 |

TABLE 7

*E. sakazakii* (ompA: 469 bp; 8.38 ± 0.25 $\log_{10}$ cells/ml)

| EMA 0 μg/ml | | EMA 10 μg/ml | | EMA 25 μg/ml | | EMA 100 μg/ml | |
|---|---|---|---|---|---|---|---|
| Live cell | Injured cell | Live cell | Injured cell | Live cell | Injured cell | Live cell | Injured cell |
| 17.6 ± 0.4[a] (2/2)[b] | 17.2 ± 0.2 (2/2) | 18.8 ± 0.3 (2/2) | 36.3, ND[c,d] (1/2) | 20.9 ± 0.6 (2/2) | ND, ND (0/2) | 23.9 ± 0.9 (2/2) | 35.0, ND (1/2) |

| EMA 0/0 μg/ml[e] | | EMA 10/10 μg/ml | | EMA 25/10 μg/ml | | EMA 100/10 μg/ml | |
|---|---|---|---|---|---|---|---|
| Live cell | Injured cell | Live cell | Injured cell | Live cell | Injured cell | Live cell | Injured cell |
| 12.9 ± 0.8 (2/2) | 17.4 ± 0.7 (2/2) | 15.9 ± 0.4 (2/2) | ND, ND (0/2) | 20.1 ± 1.6 (2/2) | ND, ND (0/2) | 23.6 ± 0.4 (2/2) | 36.0, ND (1/2) |

[a] Ct value (mean ± SD, N = 2)
[b] "(i/2)" represents the number of times of positive reaction in two PCR assays.
[c] "ND" means that final PCR amplified product is negative.
[d] "36.3, ND" means that the first Ct value is 36.3 and the second Ct value is ND.
[e] "EMA i/j μg/ml" is the results of the two-step EMA treatment and means that the first EMA treatment is performed at a concentration of i μg/ml and the second EMA treatment is performed at a concentration of j μg/ml.

TABLE 8

| | EMA 0 μg/ml + Incubation (37° C., 2 hr) + EMA 0 μg/ml | | EMA 10 μg/ml + Incubation (37° C., 2 hr) + EMA 10 μg/ml | |
|---|---|---|---|---|
| | Live cell | Injured cell | Live cell | Injured cell |
| Band intensity | 1.060 | 0.846 | 0.997 | 0.000 |

TABLE 9

| | EMA 0 μg/ml | | EMA 10 μg/ml | |
|---|---|---|---|---|
| | Live cell | Injured cell | Live cell | Injured cell |
| Band intensity | 0.834 | 0.900 | 0.845 | 0.855 |

TABLE 10

| E. sakazakii (MMS: 79 bp; 8.38 ± 0.25 $\log_{10}$ cells/ml) | | | | | | | |
|---|---|---|---|---|---|---|---|
| EMA 0 μg/ml | | EMA 10 μg/ml | | EMA 25 μg/ml | | EMA 100 μg/ml | |
| Live cell | Injured cell | Live cell | Injured cell | Live cell | Injured cell | Live cell | Injured cell |
| 19.6 ± 2.0[a] (2/2)[b] | 24.0 ± 3.5 (2/2) | 20.8 ± 0.9 (2/2) | 27.6 ± 0.1 (2/2) | 19.9 ± 1.3 (2/2) | 27.3 ± 1.0 (2/2) | 22.2 ± 1.0 (2/2) | 25.2 ± 0.5 (2/2) |
| EMA 0/0 μg/ml[c] | | EMA 10/10 μg/ml | | EMA 25/10 μg/ml | | EMA 100/10 μg/ml | |
| Live cell | Injured cell | Live cell | Injured cell | Live cell | Injured cell | Live cell | Injured cell |
| 18.0 ± 0.1 (2/2) | 23.9 ± 1.5 (2/2) | 17.1 ± 1.8 (2/2) | ND, ND (0/2) | 18.5 ± 2.5 (2/2) | ND, ND (0/2) | 22.9 ± 1.0 (2/2) | 27.3, ND[d,e] (1/2) |

[a]Ct value (mean ± SD, N = 2)
[b]"(i/2)" represents the number of times of positive reaction in two PCR assays.
[c]"EMA i/j μg/ml" is the results of the two-step EMA treatment and means that the first EMA treatment is performed at a concentration of i μg/ml and the second EMA treatment is performed at a concentration of j μg/ml.
[d]"ND" means that final PCR amplified product is negative.
[e]"27.3, ND" means that the first Ct value is 27.3 and the second Ct value is ND.

In the case where EMA was not added in the multi-step treatment, bands which were estimated as ompA gene amplified products and MMS gene amplified products were detected in both the live cells and injured cells of *sakazakii*, and it was impossible to specifically detect only live cells. However, in the case where EMA was added in the multi-step treatment (EMA 10 μg/ml-incubation-EMA 10 μg/ml), bands were clearly detected in the live cells, while no band was detected in the injured cells. (In the case of the injured cells, a band shorter than the target gene appears and is a primer dimer.) The results suggest that the multi-step treatment enables selective detection of only the live cells in PCR. As is obvious from the data obtained by quantifying the band intensities (shown in Tables 5 and 8), the multi-step treatment enables clear discrimination of the live cells from injured cells in PCR targeting the relatively and extremely short gene (469 bp and 78 bp).

According to the Ct values in Table 7, in the single-step treatment with 25 μg/ml EMA, live cells of microorganism are distinguished from injured cells of microorganism. However, the Ct value in the live cells of microorganism is 20.9±0.6, which is larger by about 5.0 than the Ct value of 15.9±0.4 in live cells treated by the multi-step treatment (EMA 10/10 μg/ml). That is, even though whether the cells are dead or live can be evaluated by the single-step treatment, it is impossible to detect a low concentration of *sakazakii* because the detection limit of live cells is lower by about 2 $\log_{10}$ cells/ml than that in the multi-step treatment.

6. Discussion

In the case of PCR targeting a very short gene, MMS gene (78 bp), as shown in Comparative Example 2, when a sample is treated with 10 μg/ml EMA by the single-step treatment, EMA passes selectively though only injured microorganism cells to directly cleave double strands of chromosomal DNA of the injured cells at many points independently of enzymes in the bacterium. However, if the number of injured cells is as high as about $10^8$ cfu/ml, the target MMS gene regions of chromosomal DNAs of all injured microorganism cells are not always cleaved. As a result, even if the concentration of EMA is high in the single-step treatment, final PCR amplified product of the injured cells does not become negative. Meanwhile, in the case where a sample is treated with EMA at a concentration equal to or less than 10 μg/ml by the single-step treatment, EMA is hard to pass through cell walls of injured cells, and chromosomal DNA is unlikely to be cleaved frequently. Therefore, in the case where the PCR target region is short, the target regions of chromosomal DNAs of all injured microorganism cells are not always cleaved, and hence, PCR is not completely inhibited.

On the other hand, after EMA is added once in the multi-step treatment, even if part of EMA passes through live cells to reduce the number of live cells, it is possible to recover the number of live microorganism cells to the initial value, to recover a diffusion pump of the live microorganism cells, or to remove unreacted EMA to the outside of the microorganism cells by incubation in a medium suitable for culture. On the other hand, although chromosomal DNA of injured microorganism cells is cleaved with EMA at many points, in the case where a gene to be amplified by PCR is short, the regions of chromosomal DNAs of all injured microorganism cells are not always cleaved. Even if the injured cells are incubated in the medium, it is impossible to increase the number of the cells unlike live cells. Under such circumstances, if EMA is added again at a certain concentration (for example, 10 μg/ml), EMA passes through only cell walls of injured cells to promote further cleavage of chromosomal DNA, and bands of final PCR amplified products may not be detected only in the case of injured cells.

Example 3

1. Preparation of Sample—Preparation of *Salmonella enteritidis* (Live Cell and Injured Cell) Suspensions A Gram-negative bacterium, *Salmonella enteritidis* (*Salmonella enteritidis* IIP 604; hereinafter, abbreviated as "*Salmonella*" in some cases), was cultured in brain-heart infusion (BHI) broth at 37° C., and 5 ml of the culture medium in the logarithmic growth phase was centrifuged at 8,000×g for 15 minutes at 4° C., followed by removal of the supernatant. 5 ml of physiological saline was added to the bacterial cells, and the whole was vigorously stirred and centrifuged while cooling in the same way as above. The supernatant was removed, and 5 ml of physiological saline was added to the bacterial cells and diluted 10-fold, to thereby prepare a live cell suspension. The number of the live cells in the live cell suspension was determined in a standard agar plate medium and found to be $8.06 \pm 0.02 \log_{10}$ cfu/ml.

The live cell suspension (1 ml) was placed in a 1.5-ml microtube, and the microtube was immersed in boiling water for 2 minutes and immediately cooled with ice water, to thereby prepare a injured cell suspension. The cells in the suspension probably include small numbers of live cells and dead cells but include mainly injured cells. Therefore, the cells are simply referred to as "injured cells". The method of the present invention is originally intended to detect live cells, and microorganism cells distinguished from live cells may be injured cells or dead cells.

2. Test Method

2-1) Multi-Step Treatment (Method of the Present Invention)

Ethidium monoazide (EMA) was added to the live cell suspension and injured cell suspension of *Salmonella* prepared above at a final concentration of 0, 10, 25, or 100 μg/ml, and the suspensions were allowed to stand under shading at 4° C. for 10 minutes. The suspensions were placed on ice and irradiated for 5 minutes with a 500-W visible light (FLOOD PRF: 100V, 500 W, IWASAKI ELECTRIC CO., LTD., wavelength: 500 to 700 nm) at a distance of 20 cm from the suspensions. Then, the suspensions were centrifuged at 15,000×g for 10 minutes at 4° C., and the supernatants were removed. An equal volume of physiological saline was added thereto, and the suspensions were stirred and centrifuged at 15,000×g for 10 minutes at 4° C., followed by removal of the supernatants. An equal volume of brain-heart infusion (BHI) broth was added thereto, and the suspensions were incubated at 37° C. for 2 hours.

EMA was not added again to the live cell and injured cell suspensions having an EMA concentration of 0 in the first EMA treatment, while EMA was added again at a final EMA concentration of 10 μg/ml to the live cell and injured cell suspensions having an EMA concentration of 10, 25, or 100 μg/ml in the first EMA treatment. The suspensions were allowed to stand under shading at 4° C. for 10 minutes, placed on ice, and irradiated for 5 minutes with a 500-W visible light at a distance of 20 cm from the suspensions.

2-2) Single Treatment (Comparative Example 3)

Ethidium monoazide (EMA) was added to the live cell and injured cell suspensions of *Salmonella* prepared in the section "1." at a final concentration of 0, 10, 25 or 100 μg/ml, and the suspensions were allowed to stand under shading at 4° C. for 10 minutes, placed on ice, and irradiated for 5 minutes with a 500-W visible light (FLOOD PRF: 100V, 500 W, IWASAKI ELECTRIC CO., LTD., wavelength: 500 to 700 nm) at a distance of 20 cm from the suspensions.

2-3) Preparation of Bacterium Suspension to be Used in PCR Test

Microtubes including one of the live cell and injured cell suspensions of *Salmonella* treated in the sections 2-1) and 2-2) above were centrifuged at 15,000×g for 10 minutes at 4° C. The supernatants were removed, and 1 ml of physiological saline was added thereto. The resultant suspensions were stirred vigorously and centrifuged while cooling in the same way as above (washing treatment). One more washing treatment was performed in the same way as the first treatment, and the same amount of sterile water as the initial amount was added to the pellets, followed by vigorous stirring.

3. PCR Targeting Invasion Gene (invA) and Enterotoxin Gene of *Salmonella* (Both of Them are Short DNAs)

3-1) Amplification of invA Gene and Enterotoxin Gene

PCR Master Mix (total volume: 25.25 μl) was prepared using Direct Buffer Mix (G&g SCIENCE CO., LTD., Yokohama, Kanagawa) capable of sequentially and automatically performing elution of chromosomal DNA from a bacterium and PCR reactions. The Buffer Mix contains: a component (surfactant) for inhibiting adsorption of a protein derived from a bacterium to a template DNA derived from a bacterium to be used in PCR reactions; and a component (surfactant) for inhibiting adsorption of a polysaccharide derived from a bacterium to a DNA polymerase; and further an ingredient necessary for real-time PCR reactions. Details of the PCR Master Mix are as follows.

Each component of PCR Master Mix for detecting invA gene is as follows.

Direct buffer MIX manufactured by G&g SCIENCE. CO., LTD.: 21 μl (5 U/μl) Ex-Taq (manufactured by TAKARA SHUZO CO., LTD, catalog No: RR001B): 0.25 μl (10 pmol/μl) invA-F DNA: 2 μl (10 pmol/μl) invA-R DNA: 2 μl invA-F: Primer Set SIN-1 for detecting invA gene of *Salmonella* (product code: S018; TakaraBio)

invA-R: Primer Set SIN-2 for detecting invA gene of *Salmonella* (product code: S018; TakaraBio)

Each component of PCR Master Mix for detecting enterotoxin gene is as follows.

Direct buffer MIX manufactured by G&g SCIENCE. CO., LTD.: 21 μl (5 U/μl) Ex-Taq (manufactured by TAKARA SHUZO CO., LTD, catalog No: RR001B): 0.25 μl (10 μmol/μl) enterotoxin-F DNA: 2 μl (10 μmol/μl) enterotoxin-R DNA: 2 μl enterotoxin-F: Primer Set STN-1 for detecting enterotoxin gene of *Salmonella* (product code:S019; TakaraBio)

enterotoxin-R: Primer Set STN-2 for detecting enterotoxin gene of *Salmonella* (product code:S019; TakaraBio)

Note that, the total amount of the above-mentioned reagents is 25.25 μl and in Direct buffer MIX manufactured by G&g SCIENCE. CO., LTD., required components for PCR Master Mix in total amount of 25.25 μl have been prepared to have the following final concentrations beforehand.

Ex-Taq Buffer (manufactured by TAKARA SHUZO CO., LTD, catalog No: RR001B): 1× dNTP mixture (manufactured by TAKARA SHUZO CO., LTD, catalog No: RR001B): 0.2 mM each SYBA Green (manufactured by BMA, catalog No: 50513): 0.4×

3-2) Thermal Cycle Profile of PCR for Amplification of invA Gene and Enterotoxin Gene

TABLE 11

Thermal cycle profile of PCR for amplification of invA gene and enterotoxin gene

| Cycle | Repeats | Step | Retention time | Hold | Set (° C.) | Temperature rising gradient (° C.) |
|---|---|---|---|---|---|---|
| 1 | 1 | 1 | 03:00 | | 4 | |
| 2 | 1 | 1 | 02:00 | | 94 | |
| 3 | 50 | 1 | 01:00 | | 94 | |
| | | 2 | 01:00 | | 55 | |
| | | 3 | 01:00 | | 68 | |
| 4 | 1 | 1 | 03:00 | | 95 | |
| 5 | 250 | 1 | 00:08 | | 70 | 0.1 |
| 6 | | | | ∞ | 4 | |

3-3) PCR Reaction

The test suspensions prepared in the section 2-3) above (2 µl each) were added to the PCR Master Mix (25.25 µl) prepared in the section 3-1) above. TE buffer (2.5 µl) was used as a negative control.

According to the PCR thermal cycle profile shown in the section 3-2), PCR reactions were performed using a real-time PCR device (iCycler, Bio-Rad Laboratories, Inc., Model: iQ).

4. Agarose Gel Electrophoresis for PCR Amplified Product

The PCR amplified products obtained in the section 3-3) above were electrophoresed on a 2% agarose gel. After completion of the electrophoresis, the agarose gel was immersed in an aqueous solution of 1 µg/ml ethidium bromide for 20 minutes and washed twice with ion-exchange water, and a UV transilluminator (wavelength: 254 nm) was used to observe the amplification degrees of the invA gene and enterotoxin gene amplified products.

5. Test Results

Figure 4:
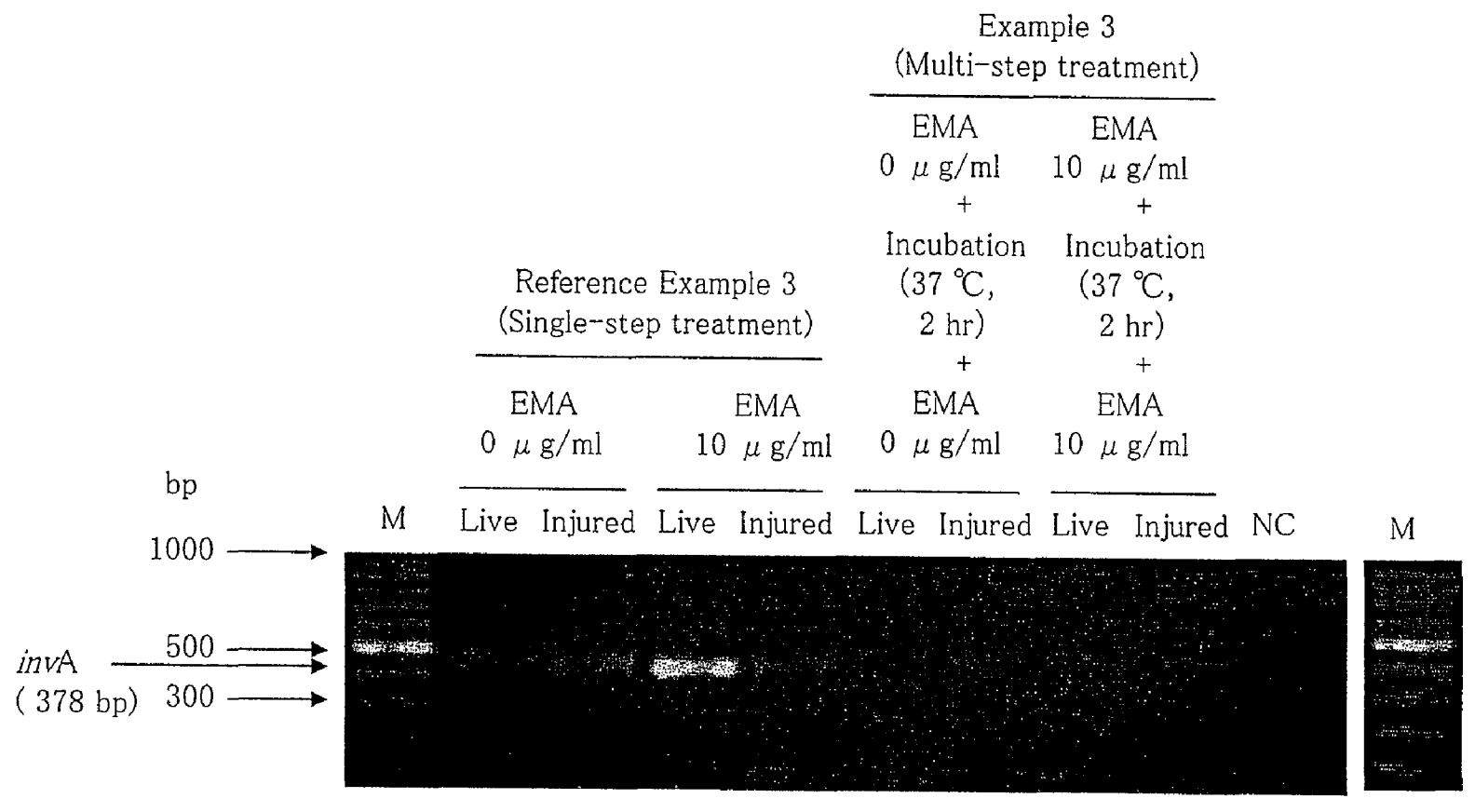

FIG. 4 shows the results obtained by performing: the multi-step treatment for the live cells and injured cells of *Salmonella*; PCR for the invA gene; and agarose gel electrophoresis (multi-step treatment lane), while Table 12 shows data obtained by quantifying band intensities of the final PCR amplified products. Meanwhile, FIG. 4 shows the results obtained by performing: the single-step treatment for the live cells and injured cells of *Salmonella*; PCR for the invA gene; and agarose gel electrophoresis (single-step treatment lane), and Table 13 shows data obtained by quantifying band intensities of the final PCR amplified products. The band intensities in the tables are values measured by scanning the color strength of each band in the electrophoresis direction using GS-700 Imaging Densitometer manufactured by Bio-Rad Laboratories, Inc. (densitometer: measurement wavelength 600 nm). Moreover, Table 14 shows the number of cycles for raising each real-time PCR curve in the multi-step treatment or single-step treatment (Ct value).

FIG. 5 shows the results of the electrophoresis for final PCR amplified products of the enterotoxin gene after the multi-step treatment (multi-step treatment lane), and Table 15 shows data obtained by quantifying the PCR bands. Meanwhile, FIG. 5 shows the results of the electrophoresis after the single-step treatment (single-step treatment lane), and Table 16 shows data obtained by quantifying the PCR bands. Meanwhile, Table 17 shows the number of cycles at initial rising in each real-time PCR curve in the multi-step treatment and single-step treatment (Ct value).

TABLE 12

| | EMA 0 µg/ml + Incubation (37° C., 2 hr) + EMA 0 µg/ml | | EMA 10 µg/ml + Incubation (37° C., 2 hr) + EMA 10 µg/ml | |
|---|---|---|---|---|
| | Live cell | Injured cell | Live cell | Injured cell |
| Band intensity | 0.777 | 1.081 | 0.742 | 0.000 |

TABLE 13

| | EMA 0 µg/ml | | EMA 10 µg/ml | |
|---|---|---|---|---|
| | Live cell | Injured cell | Live cell | Injured cell |
| Band intensity | 0.519 | 0.908 | 2.856 | 1.218 |

TABLE 14

*S. enteritidis* (invA: 378 bp; 8.07 ± 0.00 $\log_{10}$ cells/ml)

| EMA 0 µg/ml | | EMA 10 µg/ml | | EMA 25 µg/ml | | EMA 100 µg/ml | |
|---|---|---|---|---|---|---|---|
| Live cell | Injured cell | Live cell | Injured cell | Live cell | Injured cell | Live cell | Injured cell |
| 17.7 ± 3.2[a] (2/2)[b] | 16.4 ± 2.3 (2/2) | 16.2 ± 0.4 (2/2) | 31.6 ± 4.7 (2/2) | 18.2 ± 0.3 (2/2) | ND, ND[c,d] (0/2) | 27.7 ± 3.6 (2/2) | ND, ND (0/2) |

| EMA 0/0 µg/ml[e] | | EMA 10/10 µg/ml | | EMA 25/10 µg/ml | | EMA 100/10 µg/ml | |
|---|---|---|---|---|---|---|---|
| Live cell | Injured cell | Live cell | Injured cell | Live cell | Injured cell | Live cell | Injured cell |
| 13.6 ± 2.6 (2/2) | 17.5 ± 2.7 (2/2) | 16.0 ± 3.5 (2/2) | ND, ND (0/2) | 18.9 ± 2.2 (2/2) | ND, ND (0/2) | 27.9 ± 3.0 (2/2) | ND, ND (0/2) |

[a]Ct value (mean ± SD, N = 2)
[b]"(i/2)" represents the number of times of positive reaction in two PCR assays.
[c]"ND" means that final PCR amplified product is negative.
[d]"ND, ND" means that final PCR amplified product is negative in both the first and second PCR assays.
[e]"EMA i/j µg/ml" is the results of the two-step EMA treatment and means that the first EMA treatment is performed at a concentration of i µg/ml and the second EMA treatment is performed at a concentration of j µg/ml.

TABLE 15

|  | EMA 0 μg/ml + Incubation (37° C., 2 hr) + EMA 0 μg/ml | | EMA 10 μg/ml + Incubation (37° C., 2 hr) + EMA 10 μg/ml | |
| --- | --- | --- | --- | --- |
|  | Live cell | Injured cell | Live cell | Injured cell |
| Band intensity | 1.816 | 1.380 | 1.053 | 0.000 |

TABLE 16

|  | EMA 0 μg/ml | | EMA 10 μg/ml | |
| --- | --- | --- | --- | --- |
|  | Live cell | Injured cell | Live cell | Injured cell |
| Band intensity | 0.853 | 1.532 | 0.616 | 0.585 |

TABLE 17

| S. enteritidis (enterotoxin: 264 bp; 8.06 ± 0.02 $\log_{10}$ cells/ml) | | | | | | | |
| --- | --- | --- | --- | --- | --- | --- | --- |
| EMA 0 μg/ml | | EMA 10 μg/ml | | EMA 25 μg/ml | | EMA 100 μg/ml | |
| Live cell | Injured cell | Live cell | Injured cell | Live cell | Injured cell | Live cell | Injured cell |
| 26.6 ± 3.0$^a$ (2/2)$^b$ | 17.2 ± 1.5 (2/2) | 20.4 ± 5.8 (2/2) | ND, 35.1$^{c,d}$ (1/2) | 21.6 ± 4.4 (2/2) | 27.8, ND (1/2) | 24.5 ± 1.8 (2/2) | ND, ND (0/2) |
| EMA 0/0 μg/ml$^e$ | | EMA 10/10 μg/ml | | EMA 25/10 μg/ml | | EMA 100/10 μg/ml | |
| Live cell | Injured cell | Live cell | Injured cell | Live cell | Injured cell | Live cell | Injured cell |
| 12.1 ± 0.8 (2/2) | 17.2 ± 1.0 (2/2) | 13.4 ± 0.4 (2/2) | ND, ND (0/2) | 17.2 ± 0.5 (2/2) | ND, ND (0/2) | 26.7 ± 1.1 (2/2) | ND, ND (0/2) |

$^a$Ct value (mean ± SD, N = 2)
$^b$"(i/2)" represents the number of times of positive reaction in two PCR assays.
$^c$"ND" means that final PCR amplified product is negative.
$^d$"ND, 35.1" means that the first Ct value is ND and the second Ct value is 35.1.
$^e$"EMA i/j μg/ml" is the results of the two-step EMA treatment and means that the first EMA treatment is performed at a concentration of i μg/ml and the second EMA treatment is performed at a concentration of j μg/ml.

In the case where EMA was not added in the multi-step treatment, bands which were estimated as invA gene amplified products and enterotoxin gene amplified products were detected in both the live cells and injured cells of *Salmonella*, and it was impossible to specifically detect only live cells. However, in the case where EMA was added in the multi-step treatment (EMA 10 μg/ml-incubation-EMA 10 μg/ml), bands were clearly detected in the live cells, while no band was detected in the injured cells. The results suggest that the multi-step treatment enables selective detection of only the live cells in PCR. As is obvious from the data obtained by quantifying the band intensities (shown in Tables 12 and 15), the multi-step treatment enables clear discrimination of the live cells from injured cells in PCR targeting the relatively short gene (378 bp and 264 bp).

According to the Ct values in Table 14, in the single-step treatments with 25 μg/ml and 100 μg/ml EMA, live cells can be distinguished from injured cells. However, the Ct value in the live cells is 18.23±0.3 and 27.7±3.8, respectively, which is larger by about 2.2 and 1.7, respectively, than the Ct value of 16.0±3.5 in live cells treated by the multi-step treatment (EMA 10/10 μg/ml). That is, even though whether the cells are dead or live can be evaluated by the single-step treatment, it is impossible to detect a low concentration of sakazakii because the detection limit of live cells is lower by about 1 $\log_{10}$ cells/ml or 4 $\log_{10}$ cells/ml compared with that in the multi-step treatment.

6. Discussion

In the case of PCR targeting a short gene, invA and enterotoxin genes (378 bp and 284 bp), as shown in Comparative Example 3, when a sample is treated with 10 μg/ml EMA by the single-step treatment, EMA directly cleave double strands of chromosomal DNA of the injured cells at many points independently of enzymes in the bacterium. However, a higher concentration of EMA causes an increase in the Ct value in live cells, resulting in lowering the detection limit of the live cells.

On the other hand, after EMA is added once in the multi-step treatment, even if part of EMA passes through live cells to reduce the number of live cells, it is possible to recover the number of live cells to the initial value, to recover a diffusion pump of the live cells, or to remove unreacted EMA to the outside of the microorganism cells by incubation in a medium suitable for culture. On the other hand, although chromosomal DNA of injured microorganism cells is cleaved with EMA at many points, in the case where a gene to be amplified by PCR is short, the regions of chromosomal DNAs of all injured microorganism cells are not always cleaved. Even if the injured cells are incubated in the medium, it is impossible to increase the number of the cells unlike live cells. Under such circumstances, if EMA is added again at a concentration of 10 μg/ml, EMA passes through only cell walls of injured cells to promote further cleavage of chromosomal DNA, and bands of final PCR amplified products are not detected only in the case of injured cells. Moreover, as is clear from the Ct values shown in Tables 14 and 17, the multi-step treatment can improve the detection limit of live cells because the treatment includes the step of incubation in a medium, with a result that, it becomes possible to detect only a low concentration of live cells.

As described above, in all the cases where PCR was performed for a total of five short genes with a sizes of about 80 to 500 bases of Gram-negative bacteria (*Enterobacter sakazakii* and *Salmonella*) and a Gram-positive bacterium (*Listeria*) by the method of the present invention (multi-step treatment), final PCR amplified products of $10^8$ injured cells (including dead cells) were not detected, while final PCR amplified products of live cells were detected. The results reveal that the method can detect specifically live cells in milk containing a maximum of $10^5$ to $10^7$ cells/ml of injured cells and dead cells of various pathogenic bacteria. Moreover, as shown in Example 2, even if MMS gene, which is present specifically in *sakazakii* but is not always directly involved in pathogenicity, is used, the multi-step treatment enables discrimination of live cells from injured cells by PCR targeting a short gene. This suggests that the present invention is applicable not only to pathogenic bacteria but also general bacteria such as putrefactive bacteria. Therefore, the present invention can be widely applied to food sanitation inspections for Gram-negative and Gram-positive bacteria such as 0-157, *Salmonella*, *Listeria*, *Enterobacter sakazakii*, *Campylobacter jejuni*, *Staphylococcus aureus*, *Bacillus cereus*, *Clostridium botulinum*, and *Clostridium welchii*.

Blood of a patient with hepatic dysfunction due to bacteremia may contain live pathogenic bacterial cells and antibiotic-injured bacterial cells at a high concentration ($10^4$ cells/ml or more), and in such a case, the method of the present invention is expected to detect only live pathogenic bacterial cells. Meanwhile, in the case where the present invention is applied to follow-up of a treatment for a tuberculosis patient with an antituberculosis drug, expectoration is mainly used as a material for an examination. Almost all sputum samples of tuberculosis patients before the treatment contains live cells of tubercle bacilli at concentrations of $10^8$ to $10^9$ cells/g, and the samples of the patients in the latter course of the treatment contain injured cells of tubercle bacilli at concentrations of $10^7$ to $10^8$ cells/g. Under such circumstances, quantification of live cells of tubercle bacilli that can be cultured is expected as an alternative rapid culture method, and according to the present invention, it becomes possible to apply PCR to diagnosis in the therapeutic process of a tuberculosis patient.

Reference Example 1

Preparation of Test Sample from Food

On the assumption that a microorganism contaminates milk (which is a food used as a test sample of the present invention), a method of preparing the test sample is described below.

An EDTA solution and Tween 80 were added to milk at a final concentration of 1 to 5 mM, especially 2 mM and at a final concentration of 0.1 to 0.5%, especially 0.1%, respectively, and the whole was centrifuged at 10,000×g for 10 minutes at 4° C. The preparation method preferably includes: adding lipase (Sigma, E.C.3.1.1.3) at a final concentration of 10 to 20 U/ml; treating the mixture at 30 to 37° C. for 30 minutes to 1 hour; adding proteinase K (Sigma, E.C.3.4.21.64) at a final concentration of 20 U/ml; and allowing the mixture to stand for 30 minutes to 1 hour. The fat layer on the liquid surface and the aqueous layer in the middle layer were removed, and the residue was collected. The residue contains bacteria, mammary epithelial cells, and somatic cells such as bovine leukocytes. If centrifugation is performed at 10,000×g or more, the residue further contains a product obtained by incompletely degrading a micellar protein with proteinase K (incompletely-degraded micellar casein product). The incompletely-degraded casein micelle product is considered as a submicelle of α,β-casein with high hydrophobicity.

The residue was suspended in an equal volume of physiological saline to the initial volume, and the suspension was centrifuged at 100×g for 5 minutes at 4° C., followed by removal of the supernatant containing microorganisms and the like.

Reference Example 2

Preparation of Test Sample from Blood (1)

An equal volume of physiological saline was added to heparinized blood, and the whole was centrifuged at 10,000×g for 5 minutes at 4° C. The supernatant was removed to collect a residue. The residue contains bacterial cells, thrombocytes, mononuclear cells such as monocytes and lymphocytes, granulocytes, and erythrocytes.

Reference Example 3

Preparation of Test Sample from Blood (2)

An equal volume of physiological saline was added to heparinized blood, and the whole was centrifuged while cooling at 100×g for 5 minutes at 4° C. to separate the blood into plasma and blood cells (mononuclear cells such as monocytes and lymphocytes, and granulocytes and erythrocytes), followed by collection of the plasma containing microorganism cells.

Reference Example 4

Preparation of Test Sample from Blood (3)

An equal volume of physiological saline was added to heparinized blood. A sterilized test tube was filled with an equal volume of Ficoll-Paque [Amersham Biosciences K. K.; Ficoll 400: 5.7 g/100 ml, sodium diatrizoate: 9 g/100 ml, specific gravity: 1.077 g/ml], and the double-diluted heparinized blood was layered slowly while the test tube was tilted. Subsequently, the whole was centrifuged at 100×g for 5 minutes at 4° C., and the supernatant containing microorganism was collected. Before layering the double-diluted heparinized blood on Ficoll-Paque, the preparation method preferably includes: adding a solution of lipase (Sigma, E.C.3.1.1.3) at a final concentration of 10 to 20 U/ml; adding a solution of deoxyribonuclease I (Sigma, EC 3.1.21.1) at a final concentration of 10 to 50 U/ml; treating the mixture at 30 to 37° C. for 30 minutes to 1 hour; adding proteinase K (Sigma, E.C.3.4.21.64) at a final concentration of 10 to 20 U/ml; and treating the mixture at 30 to 37° C. for 30 minutes to 1 hour.

Reference Example 5

Preparation of Test Sample from Blood (4)

Monopoly™ [Amersham Biosciences K. K.; a mixture of Ficoll and Metrizoate, specific gravity: 1.115 g/ml] was added to a sterilized test tube in a half volume of the heparinized blood, and the heparinized blood was layered slowly while the test tube was tilted. Then, the whole was centrifuged at 100×g for 5 minutes at 4° C., and the supernatant containing bacteria was collected.

INDUSTRIAL APPLICABILITY

According to the present invention, live cells can be easily and rapidly distinguished from injured and dead cells in foods, biological samples, and the environment such as industrial water or tap water by the nucleic acid amplification method. The method and kit of the present invention are applicable to voluntary inspections and are excellent from an economical standpoint.

What is claimed is:

1. A method of detecting live cells by distinguishing the live cells from dead cells and also from injured cells of a microorganism in a test sample comprising the steps of:
   a) adding a cross-linker capable of cross-linking a DNA by irradiation with light having a wavelength of 350 nm to 700 nm to the test sample;
   b) irradiating the test sample to which the cross-linker is added with light having a wavelength of 350 nm to 700 nm;
   c) removing the cross-linker contained in the test sample irradiated with light;
   d) adding a medium to the test sample from which the cross-linker is removed and proliferating live cells by culture with incubation of the test sample;
   e) adding again the cross-linker capable of cross-linking a DNA by irradiation with light having a wavelength of 350 nm to 700 nm to the incubated test sample;
   f) irradiating the test sample to which the cross-linker is added with light having a wavelength of 350 nm to 700 nm;
   g) extracting a DNA from the test sample and amplifying a target region of the extracted DNA by a nucleic acid amplification method; and
   h) analyzing the amplified product.

2. The method according to claim 1, wherein the amplified product is analyzed based on a standard curve which is created by using a standard sample of the microorganism and shows a relationship between an amount of the microorganism and the amplified product.

3. The method according to claim 1, wherein the nucleic acid amplification method is a PCR, LAMP, SDA, LCR, or DNA microarray method.

4. The method according to claim 3, wherein the PCR method is performed by a real-time PCR method to simultaneously perform PCR and an analysis of an amplified product.

5. The method according to claim 1, wherein the test sample is a food, a blood sample, an urine sample, a spinal fluid sample, a synovial fluid sample, a pleural effusion sample, industrial water, tap water, groundwater, river water or rainwater.

6. The method according to claim 1, wherein the cross-linker is selected from the group consisting of ethidium monoazide, ethidium diazide, psolaren, 4,5',8-trimethyl psolaren, and 8-methoxy psolaren.

7. The method according to claim 1, wherein a length of the target region is 50 to 5,000 bases.

8. The method according to claim 1, wherein the microorganism is a pathogenic bacterium.

9. The method according to claim 8, wherein the target region is a pathogenic gene.

* * * * *

UNITED STATES PATENT AND TRADEMARK OFFICE
CERTIFICATE OF CORRECTION

PATENT NO. : 8,221,975 B2
APPLICATION NO. : 12/445506
DATED : July 17, 2012
INVENTOR(S) : Yoshida et al.

It is certified that error appears in the above-identified patent and that said Letters Patent is hereby corrected as shown below:

In column 2 (page 1 item 56) at line 12, Under Other Publications, change "Technololgies" to --Technologies--.

In column 2 (page 1 item 56) at line 15, Under Other Publications, change "Monazide" to --Monoazide--.

In Column 2 (page 1 item 56) at line 28, Under Other Publications, change "Supplementary European Search Report" to --Extended European Search Report--.

In column 3 at line 64, Change "psolaren," to --psoralen,--.

In column 3 at line 64, Change "psolaren," to --psoralen,--.

In column 3 at line 65, Change "psolaren." to --psoralen.--.

In column 4 at line 18, Change "psolaren," to --psoralen,--.

In column 4 at line 18, Change "psolaren," to --psoralen,--.

In column 4 at line 18, Change "psolaren." to --psoralen.--.

In column 6 at line 7, Change "closs-linker" to --cross-linker--.

In column 7 at line 42, Change "psolaren," to --psoralen,--.

In column 7 at line 42, Change "psolaren" to --psoralen--.

In column 7 at line 43, Change "psolaren." to --psoralen.--.

In column 8 at line 1, Change "psolaren" to --psoralen--.

In column 8 at line 3, Change "psolaren" to --psoralen--.

In column 8 at line 5, Change "psolaren" to --psoralen--.

In column 13 at line 3, Change "psolaren," to --psoralen,--.

In column 13 at line 3-4, Change "psolaren," to --psoralen,--.

In column 13 at line 4, Change "psolaren." to --psoralen.--.

In column 18 at line 26, Change "Snthesis" to --Synthesis--.

Signed and Sealed this
Twelfth Day of March, 2013

Teresa Stanek Rea
*Acting Director of the United States Patent and Trademark Office*

CERTIFICATE OF CORRECTION (continued)
U.S. Pat. No. 8,221,975 B2

In column 19 at line 34, Change "LTV" to --UV--.

In column 34 at line 18, In Claim 6, change "psolaren," to --psoralen,--.

In column 34 at line 18-19, In Claim 6, change "psolaren," to --psoralen,--.

In column 34 at line 19, In Claim 6, change "psolaren." to --psoralen,--.

SEQUENCE LISTING

<160> NUMBER OF SEQ ID NOS: 6

<210> SEQ ID NO 1
<211> LENGTH: 19
<212> TYPE: DNA
<213> ORGANISM: Artificial sequence
<220> FEATURE:
<223> OTHER INFORMATION: primer hlyA-F

<400> SEQUENCE: 1
tgcaagtcct aagacgcca                                               19

<210> SEQ ID NO 2
<211> LENGTH: 24
<212> TYPE: DNA
<213> ORGANISM: Artificial sequence
<220> FEATURE:
<223> OTHER INFORMATION: primer hlyA-R

<400> SEQUENCE: 2
cactgcatct ccgtggtata ctaa                                         24

<210> SEQ ID NO 3
<211> LENGTH: 22
<212> TYPE: DNA
<213> ORGANISM: Artificial sequence
<220> FEATURE:
<223> OTHER INFORMATION: primer ompA-F

<400> SEQUENCE: 3
ggatttaacc gtgaactttt cc                                           22

<210> SEQ ID NO 4
<211> LENGTH: 19
<212> TYPE: DNA
<213> ORGANISM: Artificial sequence
<220> FEATURE:
<223> OTHER INFORMATION: primer ompA-R

<400> SEQUENCE: 4
cgccagcgat gttagaaga                                               19

<210> SEQ ID NO 5
<211> LENGTH: 22
<212> TYPE: DNA
<213> ORGANISM: Artificial sequence
<220> FEATURE:
<223> OTHER INFORMATION: primer MMS-F

<400> SEQUENCE: 5
gggatattgt cccctgaaac ag                                           22

<210> SEQ ID NO 6
<211> LENGTH: 19
<212> TYPE: DNA
<213> ORGANISM: Artificial sequence
<220> FEATURE:
<223> OTHER INFORMATION: primer MMS-R

<400> SEQUENCE: 6
cgagaataag ccgcgcatt                                               19